(12) United States Patent
Powell et al.

(10) Patent No.: US 11,980,637 B2
(45) Date of Patent: May 14, 2024

(54) COMPOSITIONS COMPRISING NANOSILICA PARTICLES AND THEIR USE IN METHODS OF ACTIVATING T LYMPHOCYTES FOR THERAPY

(71) Applicant: United Kingdom Research and Innovation, Swindon (GB)

(72) Inventors: Jonathan Joseph Powell, Cambridge (GB); Nuno Jorge Rodrigues Faria, Milton Ernest (GB); Rachel Elaine Hewitt, Cambridge (GB); Bradley Michael Vis, Thunder Bay (CA); Carlos Bastos, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 257 days.

(21) Appl. No.: 17/233,802

(22) Filed: Apr. 19, 2021

(65) Prior Publication Data
US 2021/0338710 A1 Nov. 4, 2021

Related U.S. Application Data

(62) Division of application No. 16/324,401, filed as application No. PCT/EP2017/070183 on Aug. 9, 2017, now Pat. No. 11,007,217.

(30) Foreign Application Priority Data

Aug. 10, 2016 (GB) ..................... 1613772
Feb. 3, 2017 (GB) ..................... 1701827

(51) Int. Cl.
*A61K 33/00* (2006.01)
*A61K 9/14* (2006.01)
*A61K 31/675* (2006.01)

(52) U.S. Cl.
CPC ............... *A61K 33/00* (2013.01); *A61K 9/14* (2013.01); *A61K 31/675* (2013.01)

(58) Field of Classification Search
None
See application file for complete search history.

(56) References Cited

U.S. PATENT DOCUMENTS

| | | |
|---|---|---|
| 5,807,951 A | 9/1998 | Konishi et al. |
| 8,173,176 B2 | 5/2012 | Kamath et al. |
| 2009/0130230 A1* | 5/2009 | Stanley, Sr. ............. A61P 31/04 424/677 |
| 2011/0229577 A1* | 9/2011 | Kerek .................... A61K 33/00 424/490 |
| 2013/0149396 A1 | 6/2013 | Stanley et al. |
| 2015/0224189 A1 | 8/2015 | Weigandt et al. |
| 2016/0303228 A1 | 10/2016 | Weigandt et al. |

FOREIGN PATENT DOCUMENTS

| | | | |
|---|---|---|---|
| CN | 104825488 A | 8/2015 | |
| EP | 1371289 A1 | 12/2003 | |
| EP | 2151466 A1 | 2/2010 | |
| EP | 2125847 B1 | 6/2015 | |
| JP | 2009155262 A | 7/2009 | |
| WO | 1995021124 A1 | 8/1995 | |
| WO | 2009052090 A2 | 4/2009 | |
| WO | 2009088250 A2 | 7/2009 | |
| WO | 2015042268 A1 | 3/2015 | |
| WO | 2015121666 A1 | 8/2015 | |
| WO | WO 2015/121666 | * 8/2015 | ............. C08G 77/02 |

OTHER PUBLICATIONS

Krauskopf (Geochimica et Cosmochimica Acta, 10:1-26, 1956—Abstract only) (Year: 1956).*
An et al., "Endothelial Cells Require Related Transcription Enhancer Factor-1 for Cell-Cell Connections Through the Induction of Gap Junction Proteins," Arteriosclerosis, thrombosis, and vascular biology. 32:1951-1959 (2012).
Becker et al., "The dark side of cyclophosphamide: cyclophosphamide-mediated ablation of regulatory T cells." J Invest Dermatol., 133(6): 1462-1465 (2013).
Benezra et al., "Multimodal silica nanoparticles are effective cancer-targeted probes in a model of human melanoma," The Journal of Clinical Investigation 121(7): 2768-2780 (2011).
Benezra et al., "Ultrasmall Integrin-Targeted Silica Nanoparticles Modulate Signaling Events and Cellular Processes in a Concentration-Dependent Manner," Small, 11(14): 1721-1732 (2015).
Bradenberger et al., Particle and Fibre Toxicoloy 10:26 (2013).
Chakraborty et al. "Insights into the initiation of TCR signaling," Nature Immunology, 15: 798-807 (2014).
Crotty, "A brief history of T cell help to B cells." Nature Reviews Immunology, 15: 185-189 (2015).
Elgueta et al., "Molecular mechanism and function of CD40/CD40L engagement in the immune system." Immunological Reviews, 229:152-172 (2009).
Fathman et al. "Molecular mechanisms of CD4+ T-cell anergy," Nature Reviews Immunology, 7: 599-609 (2007).
Gao et al., "Influence of surfactant surface coverage and aging time on physical properties of silica nanoparticles," Colloids and Surfaces A: Physicochem. Eng. Aspects 350: 33-37 (2009).
Gauthy et al., "GARF is regulated by miRNAs and controls latent TGF-beta1 production by human regulatory T cells." PloS one, 8:e76186 (2013).
GB, Search Report Issued by the Great Britain Intellectual Property Office for Application No. GB1613772.1 dated Aug. 1, 2017, 6 pages.
GB, Search Report Issued by the Great Britain Intellectual Property Office for Application No. GB1701827.6, dated Nov. 17, 2017, 5 pages.
Geginat et al., "Plasticity of human CD4 T cell subsets." Frontiers in Immunology, 5(630): 1-10 (2014).
Hayashi et al., "Reductive alteration of the regulatory function of the CD4(+)CD25(+) T cell fraction in silicosis patients," International Journal of Immuno-pathology and Pharmacology, 23(4): 1099-1109 (2010).

(Continued)

*Primary Examiner* — Craig D Ricci
(74) *Attorney, Agent, or Firm* — McNeill Baur PLLC

(57) ABSTRACT

Compositions comprising silica particles having a mean size by standard particle sizing of between 0.5 nm and 20 nm are described for used in activating lymphocytes in culture or in whole blood.

20 Claims, 13 Drawing Sheets

(56) References Cited

OTHER PUBLICATIONS

Hirai et al., "Size-dependent immune-modulating effect of amorphous nanosilica particles," Pharmazie. 66(9): 727-728 (2011).
Jaganathan et al., "Biocompatibility assessment of Si-based Nano- and Micro-particles," Adv Drug Deliv Rev., 64(15): 1800-1819. (2012).
Jugdaohsingh et al., "Oligomeric but not monomeric silica prevents aluminum absorption in humans." American Journal of Clinical Nutrition, 71:944-949 (2000).
Jugdaohsingh, et al., "Is there a biochemical role for silicon?", Metal Ions in Biology and Medicine, vol. 10, pp. 45-55 (2008).
Kim et al., "Polymer Dynamics in PEG-Silica Nanocomposites: Effects of Polymer Molecular Weight, Temperature and Solvent Dilution," Macromolecules, 45: 4225-4237 (2012).
Lee et al., "Environmental factors producing autoimmune dysregulation—chronic activation of T cells caused by silica exposure," Immunobiology 217: 743-748 (2012).
Love, et al., "ITAM-mediated signaling by the T-cell antigen receptor," Cold Spring Harbor perspectives in biology, 2: a002485 (2010).
Lu et al., "In vitro cytotoxicity and induction of apoptosis by silica nanoparticles in human hepG2 hepatoma cells," International Journal of Nanomedicine 6:1889-1901 (2011).
PCT, International Search Report and Written Opinion issued by the International Searching Authority for Application No. PCT/EP2017/070183, dated Jan. 3, 2018, 12 pages.
Rossy et al., "How does the kinase Lck phosphorylate the T cell receptor? Spatial organization as a regulatory mechanism," Frontiers in Immunology, 3(167): 1-6 (2012).
Sakaguchi et al., "FOXP3+ regulatory T cells in the human immune system." Nature Reviews Immunology, 10: 490-500 (2010).
Skrastina et al., Silica Nanoparticles as the Adjuvant for the Immunisation of Mice Using Hepatitis B Core Virus-Like Particles, PLoS ONE 9(12): e114006, pp. 1-17 (2014).
Solan et al., "Connexin43 phosphorylation at S368 is acute during S and G2/M and in response to protein kinase C activation," Journal of Cell Science, 116: 2203-2211 (2003).
Sripanyakorn et al., "The comparative absorption of silicon from different foods and food Supplements." British Journal of Nutrition, 102: 825-834 (2009).
Stockis et al., "Membrane protein GARF is a receptor for latent TGF-beta on the surface of activated human Treg." European Journal of Immunology, 39: 3315-3322 (2009).
Ueki et al., "Polyclonal human T-cell activation by silicate in vitro," Immunology, 82: 332-335 (1994).
Vis et al., "Non-Functionalized Ultrasmall Silica Nanoparticles Directly and Size-Selectively Activate T Cells." ACS Nano 12: 10843-10854 (2018).
Wang et al. "Comprehensive Mechanism Analysis ofMesoporous-Silica-Nanaparticle-Induced Cancer Immunotherapy," Advanced Healthcare Materials 5(10): 1169-11I76 (2016).
Wang et al. "Stimulation of in vivo antitumor immunity with hollow mesoporous silica nanospheres". Angewandte Chemie International Edition, 55:1899-1903 (2016).
Wang et al., "ZAP-70: an essential kinase in T-cell signaling," Cold Spring Harbor perspectives in biology, 2:a002279 (2010).
Knossalla et al., "Continuous synthesis of nanostructured silica based materials in a gas-liquid segmented flow tubular reactor," New J. Chem. 40:4361-4366 (2016).
Vallhov et al., "Adjuvant Properties of Mesoporous Silica Particles Tune the Development of Effector T Cells," Small 8(13):2116-2124 (2012).
Examiner's Report issued in JP 2019-507262, dated Nov. 30, 2022.
Final Office Action issued on JP 2019-507262 dated Apr. 21, 2022, 4 pages.
Functional materials of Nissan Chemical, Features of inorganic colloid, Jun. 2016, 3 pages.
Saito et al., "Two FOXP3+CD4+ T cell subpopulations distinctly control the prognosis of colorectal cancers," Nature Medicine vol. 22, pp. 679-684, Abstract only (2016).
Notice of Reason(s) for Rejection issued on JP 2022-132004 dated Jul. 28, 2023.
Regulatory T cells were involved in the progression of colorectal cancer!—Expectations for colorectal cancer treatment by controlling intestinal bacteria—, Jun. 1, 2016, available at web.archive. org/web/20160601142608/https://www.amed.go.jp/news/release_20160426.html.

* cited by examiner

COMPOSITIONS COMPRISING NANOSILICA PARTICLES AND THEIR USE IN METHODS OF ACTIVATING T LYMPHOCYTES FOR THERAPY

CROSS-REFERENCE TO RELATED APPLICATIONS

This application is a divisional of U.S. application Ser. No. 16/324,401, filed Feb. 8, 2019, which is a national phase entry pursuant to 35 U.S.C. § 371 of International Application No. PCT/EP2017/070183, filed Aug. 9, 2017, which claims priority of United Kingdom Patent Application No. 1613772.1, filed Aug. 10, 2016, and United Kingdom Patent Application No. 1701827.6, filed Feb. 3, 2017, each of which is incorporated herein by reference herein in its entirety for any purpose.

FIELD OF THE INVENTION

The present invention relates to compositions comprising nanosilica particles and their use in methods of activating T lymphocytes for therapy, and in particular to biomarkers that characterise the effectiveness of silica particle compositions for use in therapy. Assays and screening methods based on the use of these markers are also disclosed, as are devices and kits for producing and/or delivering nanosilica compositions or T lymphocytes that have been activated ex vivo prior to being administered to a subject.

BACKGROUND OF THE INVENTION

Silicon is an environmentally ubiquitous element and adult humans in the Western world ingest about 15 to 50 mg per day currently. Naturally it occurs as silicates wherein silicon links to oxygen atoms. Silicic acid and silica are also terms used for such structures. These range from the simplest mono silicic acid, also termed ortho, to silica particles. Herein the term silicate and silica may be used interchangeably to mean silicon, oxygen and hydrogen containing materials that may also contain other ions but are predominantly silicon and oxygen containing with hydrogen content determined by factors such as size, extent of condensation, pH etc. The precise biological role of soluble silicate is not yet understood but much evidence points to an important role in connective tissue health (Jugdaohsingh et al., 2008). Whilst quintessential connective tissues include bone, joints, blood vessels, skin, hair and nails, there is also notable evidence for dietary, supplemental, or therapeutic benefit of soluble or polymeric silicate in a wide array of medical conditions that include osteoporosis, osteopenia and other musculoskeletal and joint disorders, cancers of all types, various skin conditions, vascular, cardiovascular and coronary heart diseases, inflammatory diseases, autoimmune diseases, Alzheimer's disease and varying forms of cognitive impairment, infections of various types, wounds and ulcers, gastrointestinal, liver, kidney and immune related disorders and hormone related changes and disorders. Beneficial nutritional and therapeutic effects of silicate appear to extend to other animals, especially other mammals.

Silicate has been used as an oral nutritional supplement, although achieving a formulation that allows effective acquisition (absorption) following dosing is not straightforward. Silicon in its naturally occurring inorganic form is soluble as orthosilicic acid. However, its concentration, e.g. in drinking water, needs to be relatively low (≤1.7 mM) as, under natural conditions, this is the maximum equilibrium solubility of aqueous silicate at pHs<9 to prevent the onset of polymerisation of particles that gradually condense and/or increase in size and then are not easily re-solubilized. This behaviour has bedevilled the development of supplemental silicon as concentrated forms do not dissolve in the gut to enable absorption, whilst dilute forms result in large quantities of supplement (e.g. 20-100 ml/day) needing to be ingested.

Normally, certain chemical moieties such as ligands may be used to bind and render soluble cations/anions that otherwise would precipitate at physiological pH, but silicate is awkward because the monomer typically has greater affinity for itself (i.e. to undergo self-assembly) than for any other molecules, and the higher the concentration of silicon the more difficult it becomes to arrest its self-assembly in aqueous solution. This has led to alternate strategies for producing bioavailable silicate compositions.

Additionally, however, either purposefully or accidentally, researchers have studied the biological effects of precipitated silicate compositions. For example, the effects on cells of polymeric, nanosized and micron sized silicates have been investigated.

US 2011/0229577 (Kerek) discloses silicic acid particles having shell-like structures in which the particles condense under conditions in which the pH of the reaction mixture is first reduced and then increased, leading to a composition said to be at a pH 2.1 or a pH greater than 9.2. The condensed silicates compositions described in US 2011/0229577 are described as having low toxicity on in vitro cell cultures as well as being inhibitors of the calcium ATPase pump and causing apoptosis in all cell types. The use of such condensed silicates for reducing the size of tumours is reported.

Silica compositions that are stabilised from agglomeration by high levels of choline are sold as a food supplement and referred to as 'choline stabilised orthosilicic acid' (Biosil™; choline chloride stabilized ortho-silicic acid, see WO 95/21124 and EP 1 371 289 A).

US 2009/0130230 (Stanley) describes silicate compositions and their uses for treating inflammatory conditions, cancer, bacterial and viral infections and the treatment of infected and uninfected wounds. This reference hypothesizes that the treatments occur via activation of the innate immune system.

WO 2015/121666 (Medical Research Council) discloses nanosilica compositions that include stabilising agents such as polyols, sugars and/or quarternary ammonium salts, such as choline and carnitine. In particular, WO 2015/121666 provides processes for producing a stabilised polymeric silicate composition comprising polymeric silicic acid and nanosilica particles, in which polymerisation of silicates and particle size growth is controlled and the resulting particles are rendered size stable through the combination of silicate concentration, pH and/or stabiliser. The uses of these compositions for the treatment of a range of medical conditions and for silicon supplementation are described.

T lymphocytes are cells of the adaptive immune system directly responsible for both orchestrating (CD4+ T helper cells) and executing (CD8+ Cytotoxic T cells) the removal of infected and cancerous cells from the body. As such, they are a vital part of the immune system. Polyclonal human T-cell activation by silicate in vitro was first reported in 1994 (Ueki et al., 1994), and despite ongoing associations of silicates with T cell activation in conditions such as silicosis, the size, structure, extent of T cell interactions and mechanism of action defining silicate and T cell interactions remain elusive (Hayashi et al., 2010, Lee et al., 2012, Kusaka et al., 2014).

SUMMARY OF THE INVENTION

Broadly, the present invention is based on the findings that compositions comprising silica particles, also termed polymeric silica or silica polymers, in particular silica structures having a mean size by standard particle sizing of between 0.5 nm and 20 nm, may be used to activate lymphocytes in culture or in whole blood. This newly observed technical effect opens up the possibility of T cell activation to be used as a marker and biomarker for the efficacy of silica treatment for cancer, infection and other chronic disease. Without wishing to be bound by any particular theory, the present inventors believe that the silica particles bind to T cell receptors, partially activating them, for example as detectable by increasing CD69 and/or CD25 expression. This means that the T cells are activated when they meet their cognate antigen (e.g. of a cancer cell or infected cell). This means that the T cells are less likely to be quiescent and the activation may therefore serve to overcome T cell exhaustion induced in cancers or certain chronic diseases, in both veterinary and human medicine.

Conventionally, primary particles of less than 100 nm diameter in one direction are loosely termed "nano" even though, by volume, this may span one million fold between 1 and 100 nm. Moreover, most researchers focus on aggregates and agglomerates that are simply "nanostructured". Truly dispersed nanoparticles are less well studied and those under 10 nm in diameter (i.e. in the range of protein sizes) have received relatively little attention in biomedical applications. For example, extensive studies have found that silica particles (—Si—O—Si—, and termed $SiO_2$ in their most condensed form) display differential cell activities depending on size and crystallinity ranging from benign activity for amorphous (poorly condensed) large particles to strongly pro-inflammatory for crystalline quartz—an effect that is partially mimicked by nanosilica irrespective of crystallinity. Few studies, however, exist on ultrafine silica particles (less than 10 nm diameter). Despite the paucity of data, ultrafine silica particles are ubiquitous, as their formation occurs when concentrations of aqueous momomeric $Si(OH)_4$ exceeds ca. 1.7 mM total [Si]. Using such 'supersaturated' silicate preparations Stanley et al teach that cancers may be treated with the resulting mixture. Kerek repeats that ultrafine silicate particles may be useful in the treatment of cancers and lists a number of potential ways for their synthesis.

Accordingly, in a first aspect, the present invention provides a composition comprising silica particles having a mean diameter between 0.5 and 20 nm for use in a method of activating T lymphocytes for therapy for a subject/individual, wherein activation of the T lymphocytes is characterised by an increase in expression of CD69 and/or CD25 by the T lymphocytes. By way of example, preferably the increase in expression of CD69 and/or CD25 is by at least 20%, by at least 30%, by at least 40%, by at least 50%, by at least 60%, by at least 70%, or by at least 80%, for example as compared to unstimulated baseline control. Cellular assays for determining CD69 and/or CD25 expression using peripheral blood mononuclear cells (PBMC) are described in the examples provided below, although alternative assays for these biomarkers will be apparent to those skilled in the art.

Generally, the present inventors have found that the T lymphocyte activation can be achieved using the silica particle compositions described herein, but not the compositions described in the prior art, such as compositions made according to the teachings of Kerek (supra) or choline-stabilized orthosilicic acid (Biosil™).

Generally, the T lymphocytes activated by contact with the nanosilica compositions used in the present invention are T cells such as T helper cells, cytotoxic T cells, cytotoxic natural killer T cells or gamma delta T cells. This is supported in experiments using T helper (CD4+) and cytotoxic (CD8+) T cells. Alternatively or additionally, T lymphocyte activation increases expression of one or more further markers of T cell activation selected from CD40L, LAP/GARP and/or FoxP3.

CD25 (Cluster of Differentiation 25) is the alpha chain of the IL-2 receptor. It is a type I transmembrane protein present on activated T cells.

CD69 (Cluster of Differentiation 69) is a human transmembrane C-Type lectin protein. The activation of T lymphocytes and Natural Killer T (NKT) Cells, both in vivo and in vitro, induces expression of CD69.

CD40 ligand or CD40L, also called CD154, is a protein that is primarily expressed on activated T lymphocytes and is a member of the TNF superfamily of molecules.

GARP (Glycoprotein A Repetitions Predominant) also known as LRRC32 (Leucine Rich Repeat Containing 32) is a protein that is essential for the surface expression of latent TGF-β on platelets and activated FOXP3$^+$ regulatory T cells. Increased expression of GARP and Latency-associated peptide (LAP) are indicators of the activation and expansion of regulatory type T lymphocytes (Treg).

FoxP3 (Forkhead box P3), also known as scurfin, is a protein involved in immune system responses. A member of the FOX protein family, FOXP3 appears to function as a master regulator of the regulatory pathway in the development and function of regulatory type T cells (Treg).

Alternatively or additionally, in some cases, lymphocyte activation may be identified by an increase in expression of IFN-γ. The experiments described herein further show that while the compositions cause lymphocyte activation, they substantially do not induce lymphocyte cell proliferation.

As well known in the art, there is an equilibrium between soluble silicic acids and increasingly condensed silicate compositions. Accordingly, in the present invention, "stabilised polymeric silicate composition" includes polymeric silicic acid and nanosilicate particles having the properties described herein, as well as soluble forms of silicic acid and polysilicic acid that they are in equilibrium with in the composition or in a formulation comprising it.

Evidence is emerging in the art that suggests that silicic acid is beneficial for health and disease prevention or cure in humans and other animals. In general, the compositions of the present invention comprise polymeric silicate compositions in which the natural tendency of nanosilicates to grow to form higher order polysilicates and silicate particles is inhibited by the inclusion of substances such as organic compounds that are capable of acting as growth retardants, i.e. which inhibit the natural tendency of polysilicic acid to grow to form gels and more condensed silicate particles or polymers and particles larger than those of the desired size. Moreover, in some aspects, the present inventors have found that this approach means that the compositions are stable at physiological acceptable pHs, especially neutral or mildly acidic pH or mildly alkaline pH.

A further advantage of the method described herein is that through the selective control of pH, silicon concentration, and stabiliser concentration during the synthesis, the particle size may be tailored from small polymers of less than 0.5 nm diameter up to 10 or 20 nm diameter depending upon the desirable particle size and that this may then be stabilised according to the invention outlined to enable administration to a subject or animal at the chosen particles size. It will be clear to those skilled in the art that a particle size refers to a range of sizes and the number quoted herein refers to the average diameter, most commonly mean diameter of that range of particles.

In a further aspect, the present invention provides the use of a composition comprising silica particles having a mean diameter between 0.5 and 20 nm in the preparation of a medicament for activating T lymphocytes for therapy for a subject/individual, wherein activation of the T lymphocytes is characterised by an increase in expression of CD69 and/or CD25 by the T lymphocytes.

In a further aspect, the present invention provides method of determining the effectiveness of a silica particle composition for therapeutic administration to a subject or individual, the method comprising:
(a) contacting a sample of T lymphocytes with the silica particle composition;
(b) determining the expression of CD69 and/or CD25 by the T lymphocytes present in the sample; and
(c) identifying the silica particle compositions that cause an increase in the expression of CD69 and/or CD25 by the T lymphocytes as being suitable for use in therapy.

In a further aspect, the present invention provides an assay for determining the effectiveness of a silica particles composition for therapeutic administration to a subject or individual, the assay comprising:
(a) contacting a sample of T lymphocytes with the silica particle composition;
(b) determining the expression of CD69 and/or CD25 by the T lymphocytes present in the sample;
(c) measuring or quantifying the amount of CD69 and/or CD25 expression to a control value, and if the amount of CD69 and/or CD25 expression is increased relative to the control value, selecting the silica particle composition as suitable for therapeutic administration.

In a further aspect, the present invention provides a method for determining the effectiveness of a therapy that comprises administration of a silica particle composition, or protocol of administration thereof, to the subject or individual, the method comprising:
(a) contacting a sample of T lymphocytes from the subject or individual treated with the silica particle composition, or protocol of administration thereof;
(b) determining the expression of CD69 and/or CD25 by the T lymphocytes present in the sample; and
(c) identifying a subject or individual for whom an increase in the expression of CD69 and/or CD25 by the T lymphocytes is observed in step (b) as being successfully treated with the silica particle composition, or protocol of administration thereof; or
(d) identifying a subject or individual for whom no increase in the expression of CD69 and/or CD25 by the T lymphocytes is observed in step (b) and modifying the silica particle composition, or protocol of administration thereof, provided to that subject or individual;
(e) optionally repeating steps (a) to (d) until the subject or individual is successfully treated with the silica particle composition, or protocol of administration thereof.

In the assays and methods set out herein, the increase in the expression of CD69 and/or CD25 by the T lymphocytes is determined relative to a reference value, for example unstimulated baseline control.

In a further aspect, the present invention provides the use of the expression of CD69 and/or CD25 by T lymphocytes as markers or biomarkers for the therapeutic effectiveness of silica particle compositions.

In a further aspect, the present invention provides a device for producing a silica composition for therapeutic use, the device comprising:
a first container comprising a silicate solution at pH>10.5, a second container comprising an acidic buffer solution;
flow control means for controlling the flow of the silicate solution and the acidic buffer solution; and
an outlet in fluid communication with the first and second containers for delivering the colloidal silica composition so that the two solutions mix prior to administration to a subject.

In one embodiment, the device is used for the batch synthesis of the silica composition and further comprises a mixing chamber in fluid communication with the first and second containers for mixing the solutions to produce a colloidal silica composition. Alternatively, where the device is for the flow synthesis of the silica compositions of the present invention, mixing of the solutions may occur in situ as they are delivered, for example in an i.v. line prior to administration to a subject.

In a further aspect of the present invention, the device may be adapted for ex vivo T lymphocyte therapy. In this aspect, the device may further comprises a chamber for contacting a biological sample comprising T lymphocytes obtained from a subject with the colloidal silica composition to cause activation of the T lymphocytes for therapy and/or means for delivering the sample comprising T lymphocytes extracted from the subject to the contacting chamber and for returning the activated T lymphocytes to the subject.

In a further aspect, the present invention provides a kit comprising (i) a first container comprising a silicate solution at pH>10.5 and (ii) a second container comprising an acidic buffer solution and (iii) instructions for mixing the silicate solution and acidic buffer solution to produce a therapeutically active colloidal silica composition having a pH between 4.0 and 8.5, more preferably 4.0 to 6.5. Preferably, the acidic solution comprises hydrochloric acid, a carboxylic acid such as citric acid, or an acidic amino acid such as glycine.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Figure 1:
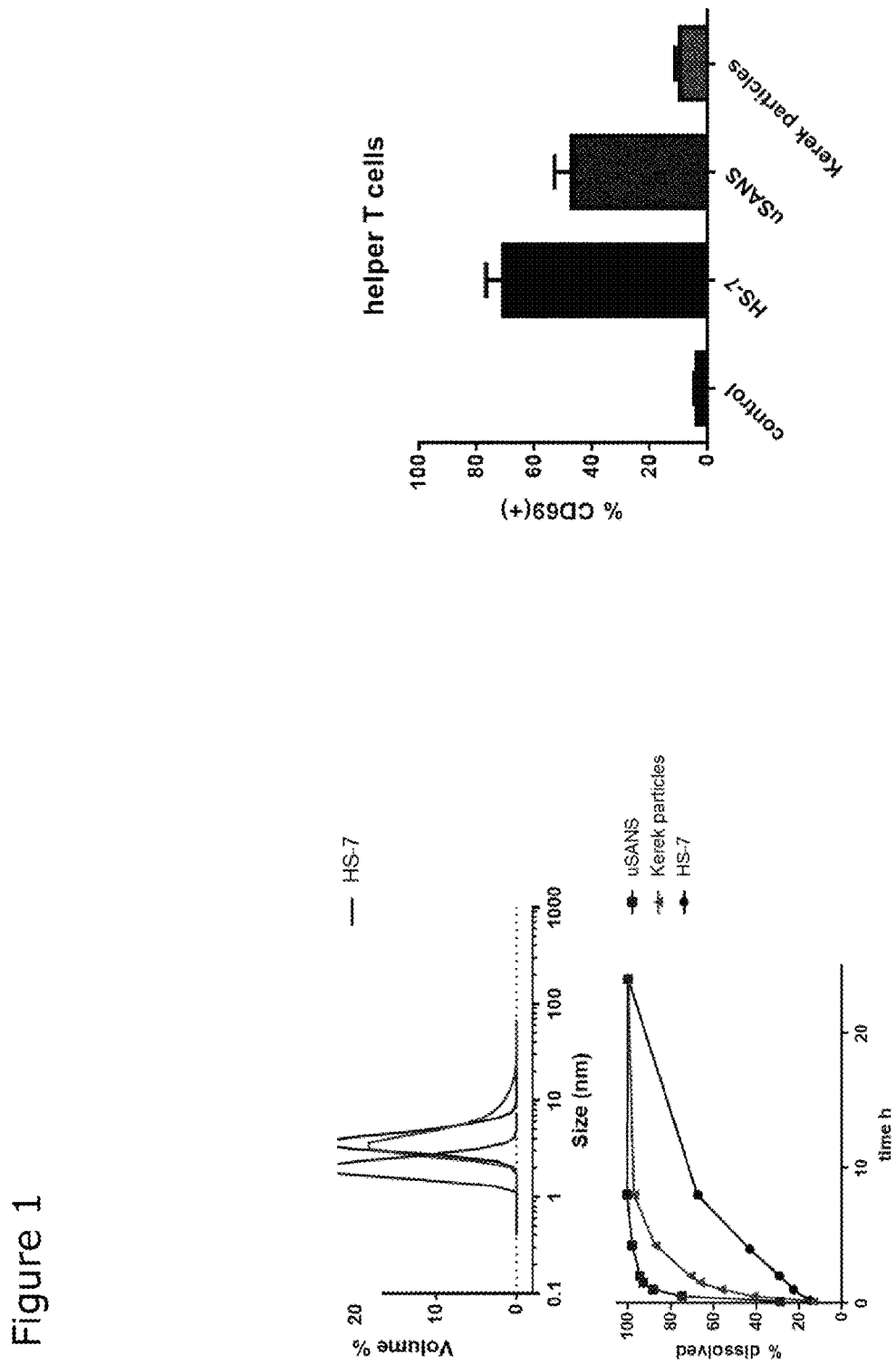
FIG. 1. T cell activation by silica particle compositions of the present invention and nanosilica particles synthesized according to Example 4 (Si(OMe)$_4$) of Kerek (US 2011/0229577). Cells were treated with the nanoparticles and activation was assessed after 24 h.

The Biological Role of Silicon and the Chemistry of Silicates

Evidence suggests that silicic acids whether monomeric or polymeric are beneficial for health and disease prevention or cure in humans and other animals. However, as described above, the fundamental problem in the art is that silicic acid, the monomer of which is represented as $Si(OH)_4$, self assembles and at pHs≤9.0 and concentrations above the maximum solubility of aqueous silicate (1.7 mM at 25° C., see FIG. 1 of Jugdaosingh et al., supra) it forms insoluble species. As is well known in the art, there is an equilibrium between soluble silicic acids and increasingly condensed silicate species, namely mono-, di- and tri-silicic acids, polysilicic acids and nanosilica particles. The process of growth from solutions of silicic acid involves evolution where the single unit grows in size and becomes more and more evolved (i.e. less labile, soluble and/or dissolvable) and, thus, less able to return towards $Si(OH)_4$ in the absence of added alkali. Growth can include polymerisation, agglomeration, aggregation or an increase in size due to surface deposition of soluble species. The growth of polysilicic acids eventually leads to gel formation under suitable conditions. These factors make it extremely difficult to stabilise silicate compositions above these concentrations of aqueous silicate and at physiologically relevant pH.

The dosing of silicate is therefore a challenge because the dosage must deliver silicon as required for a desirable effect in terms of both concentration and chemical form, and at a pH that is compatible with physiological health and in a manner that will avoid persistent nanoparticles of silicate that may have adverse effects to health. Of particular note is that during application of a dosage, three notable changes generally occur due to the physiological environment. Firstly, there will be dilution by the physiological fluids, and secondly there will be a pH change, and thirdly there will be a change in the ionic strength. The net effect of these influences will determine the behaviour of the dosed silicate.

Nanosilica Compositions and T Lymphocyte Activation

We have found that the nanosilica compositions of the present invention, and more preferably ultrafine nanoparticles of silica (<10 nm in diameter), can stimulate T lymphocyte activation as measured, for example, by an increase on the T lymphocyte surface of the markers CD25 and CD69. Whilst not wishing to be bound by any particular theory, the present inventors believe that this occurs through direct binding of the nanosilica to the CD3-T lymphocyte receptor complex (herein referred to as CD3-TCR complex). Importantly, although size appears to be one predictor of whether nanosilica compositions are capable of activating T lymphocytes, other factors may contribute to this property. For example, ultrafine nanoparticles of silica that are stabilised from agglomeration by high levels of choline are sold as a food supplement and referred to as 'choline stabilised orthosilicic acid' (Biosil™; choline chloride stabilized ortho-silicic acid, see WO 95/21124 and EP 1 371 289 A), yet these were not able to stimulate T lymphocyte activation in our assays (see FIGS. 2 and 5). In another example, nanosilica reported by Kerek (US 2011/0229577), prepared by way of comparison in Example 4 herein, was a very weak activation inducer of CD4 T lymphocytes and a modest inducer of CD8 T lymphocyte activation compared to some freshly precipitated nanosilicas prepared by pH adjustment of alkaline solutions of silicate salts (see FIGS. 1, 3 and 4). A further example is that the sucrose stabilised nanosilica particles reported in WO2015/121666 were able to activate CD4 and CD8 T lymphocytes in the same manner as non-stabilised particles. Thus, in one aspect, the present invention provides an assay for determining the effectiveness of a silica particle composition for stimulating T lymphocytes as this is not obvious from simple physicochemical determinations. In turn, this may allow the activity of a silica nanoparticle to be chosen, including any desirable differential effects on CD8 and CD4 T lymphocytes which may allow better targeted T lymphocyte activation therapy.

Notwithstanding, the inventors have also found that specific sub-types or 'lineages' of T lymphocytes may be simultaneously activated by their exposure to the ultrafine nanosilica. For example, CD4+ T helper (Th) cells may be conveniently divided into a number of different Th lineages depending upon the type of immune response that they are involved in regulating (Geginat et al., 2015). So called Th1 CD4+ helper cells might mediate a cytotoxic T lymphocyte response and activate monocytes and they are characterized by the production of IFN-γ (Geginat et al., 2015). Whereas, so called regulatory CD4+ T helper cells (Treg) are responsible for suppressing immune responses and these can be identified by the foxhead box P3 (FoxP3) protein and the surface expression of LAP and GARP (Sakaguchi et al., 2010, Gauthy et al., 2013; Stockis et al., 2009). Whereas, so called Th2 CD4+ T helper cells might be responsible for mediating B cell responses, for example. CD40Ligand, also termed CD154, might be expressed on Th2 cells and engage the CD40 receptor of B cells, facilitating B cell proliferation and survival (Crotty, 2015; Elgueta et al., 2009).

Figure 8:
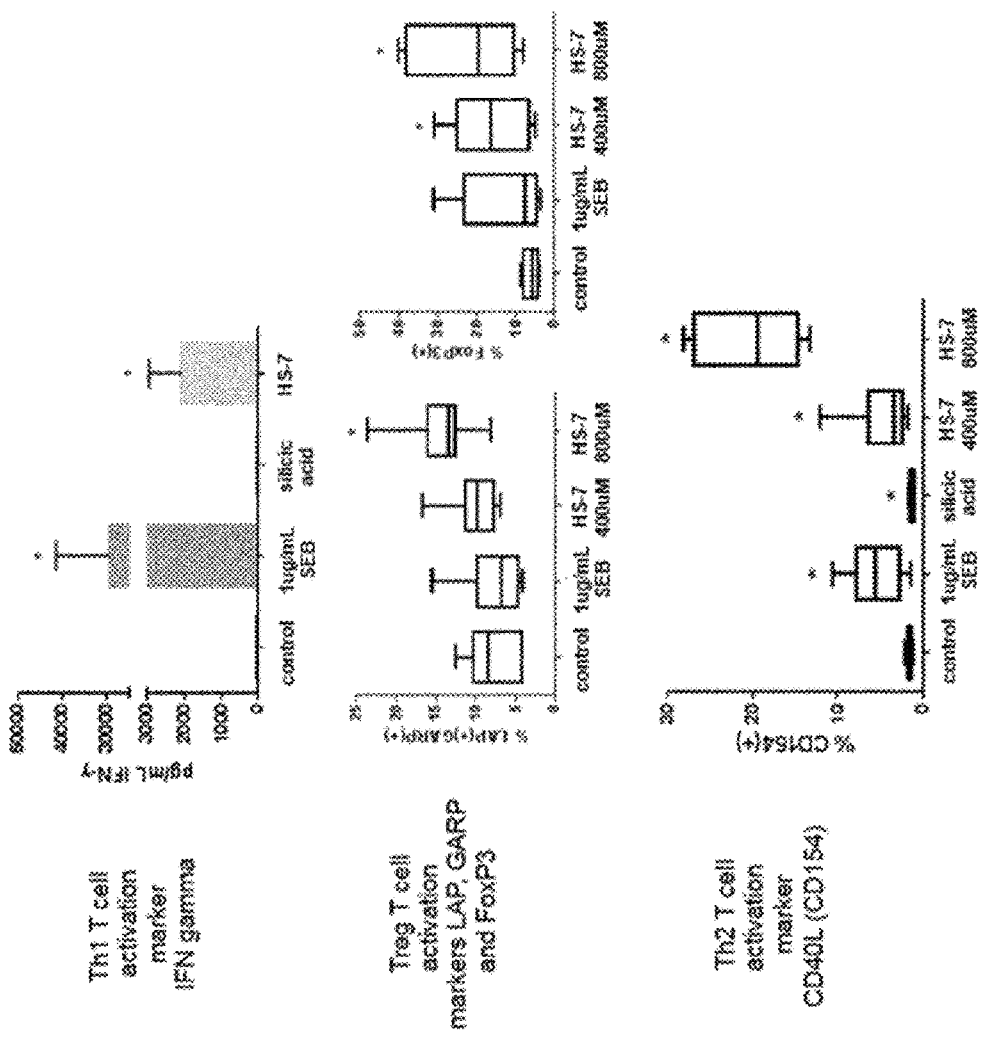
FIG. 8. The activation of different Th lineage cell types by ultrafine nanosilica that is termed 'HS-7' and prepared by pH neutralisation (pH 7) of an alkaline sodium silicate solution to a final concentration of 23 mM Si and incubated for ~20 h prior to addition to cell cultures (n=6-7). Particles had a mean diameter (DV 0.5)=3.4-3.8 nm from repeat analyses.

The present inventors have found that T lymphocytes of multiple lineage types may be susceptible to T lymphocyte activation via these ultrafine nanosilica particles (FIG. 8). This allows the T lymphocytes to be employed in a number of therapeutic applications. First, the assay may be used to identify specific types/forms of nanosilica that select or polarise this effect towards one lineage of T lymphocyte, such that regulatory, Th1 or Th2 could be preferentially selected through treatment. For example, selective activation of Th1 cells may be desirable for cancers or viral disease. Selective activation of Tregs may be desirable for autoimmune or inflammatory disease.

Secondly, with chronic dosing, the activation of T lymphocytes may be used therapeutically to achieve 'exhaustion', in other words the reverse of activation, and thus the dampening (de-activation) of all, or indeed selected, T lymphocyte types. For example, this may be therapeutically helpful in 'inflammatory disease' irrespective of whether classical auto-immune such as multiple sclerosis or rheumatoid arthritis, classical Th1 such as Crohn's disease or rheumatoid arthritis, or Th2 such as asthma or ulcerative colitis. Auto-immune diseases may have Th1 or Th2 polarisation, hence rheumatoid arthritis is mentioned twice.

Thirdly, the use of silica particles to activate or exhaust all or selected T lymphocytes may be used in-conjunction with co-administration of therapy that suppresses or enhances a specific T cell lineage or phenotype, thereby selecting the type of response. For example sequestration of T reg T lymphocyte lineage for cancer therapy by cyclophosphamide (Becker et al., 2013), thus allowing selected 'growth' of effector T lymphocytes lineages with nanosilica therapy that could be implemented in a regimen that avoids chronic T lymphocyte exhaustion. Co-administration for such purposes may be before and/or during and/or after the administration of the nanosilica and may involve one or more agents.

Figure 9:
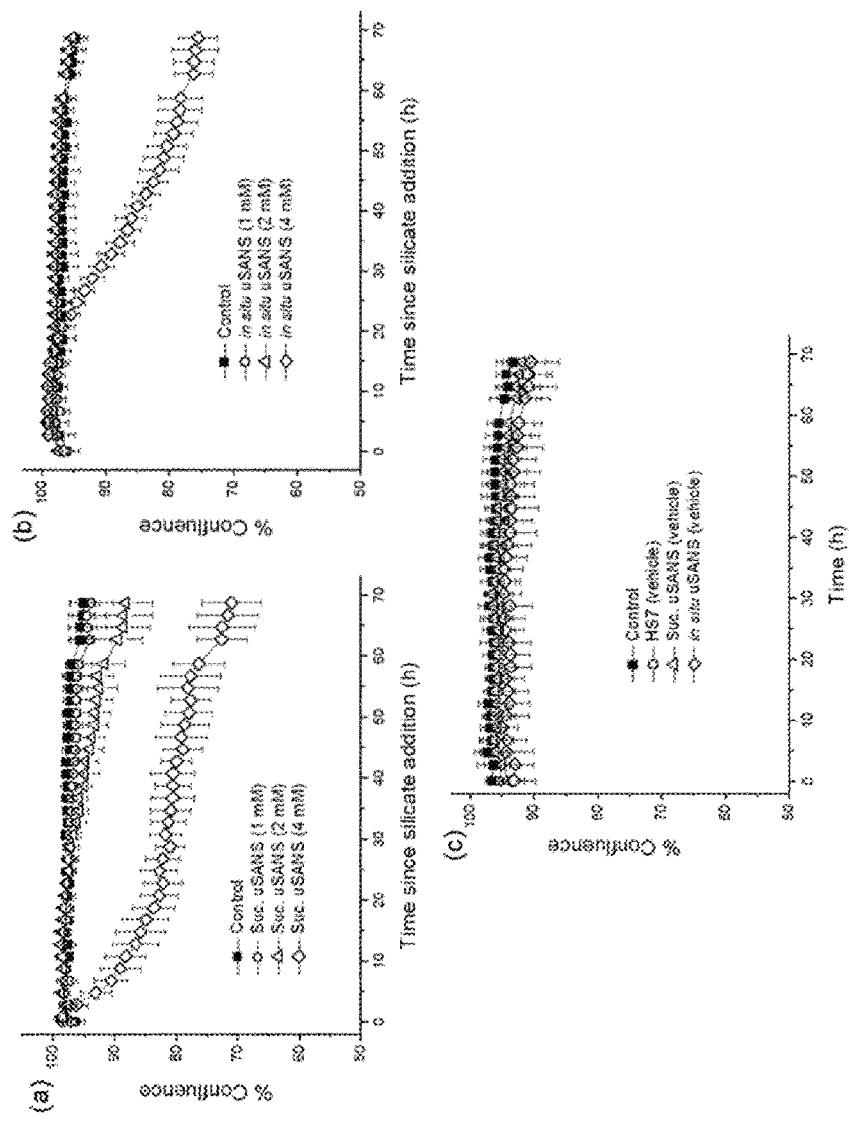
FIG. 9. Effect of suc. uSANS (a), in situ uSANS (b) and their vehicle controls (c) on the confluence of HUVEC cells. Note data cannot be shown for the third nanosilica studied, termed HS7, because it induced cellular toxicity (i.e. a change in cell shape and/or cell death), after a short period of incubation (<1 h) at all three concentrations (1, 2 and 4 mM Si) and after 4-5 h incubation most of the cells had died at the 4 mM concentration. In follow on experiments with lower concentrations of HS7 (0.1, 0.25 and 0.5 mM Si) there was toxicity even at 0.5 mM Si.
Figure 10:
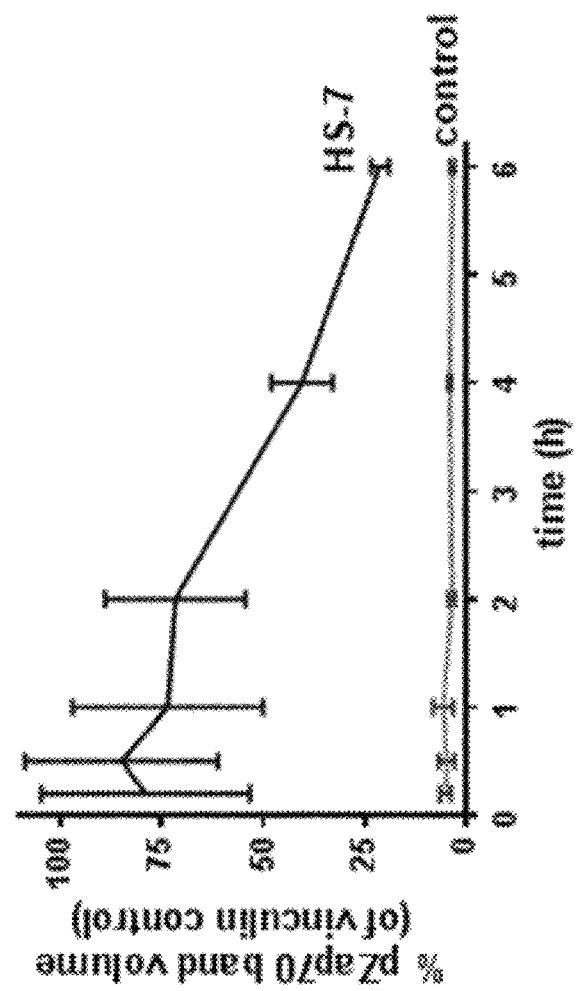
FIG. 10. pZap70 measured over time demonstrates the rapid activation of T cells which originates from nanosilica interacting with the T cell receptor, which leads to the phosphorylation of ZAP-70.

It will be desirable to deliver therapeutic nanosilica parenterally as little is absorbed from the gastrointestinal tract (Jugdaohsingh et al., 2000). It is recognised that intravenous administration may be especially desirable (WO 2015121666). However, this would require the nanosilica, which may be injected at high concentrations to achieve effective therapeutic doses in the blood stream, to be minimally toxic to the endothelial cells lining the vascular system. Indeed, so called uSANS particles, a form of nanosilica, disclosed in WO 2015/121666 are minimally persistent and thus are less toxic to endothelial cells than those previously disclosed in US 2009/0130230 by Stanley (herein referred to as HS7 particles). HS 7 particles are comparatively more toxic above 0.5 mM Si thus reducing their clinical application at therapeutic doses. However, despite being better tolerated than HS7 particles, uSANS particles still exhibit moderate toxicity to endothelial cells (FIG. 9). However, the inventors have discovered that there is a very rapid interaction of nanosilica particles with the TCR, as demonstrated by the rapid phosphorylation of the Zeta-chain-associated protein kinase 70 (pZap70) of T lymphocytes by nanosilica (FIG. 10), and this means that extra-corporeal treatment of blood or isolated cells is a useful method to deliver the nanosilica. In particular, cells, either with a degree of isolation from their tissue or biofluid, or as present in whole blood, need not be out of the body for a long time and can then be treated with nanosilica and re-injected for therapeutic use. This would spare endothelial damage as immune cell and protein binding by the nanosilica, and some dissolution of the nanosilica particles, would minimise endothelial cell interactions and damage by the nanosilica upon its re-administration.

Accordingly, in one aspect, the present invention provides a composition comprising silica particles having a mean diameter between 0.5 and 20 nm for use in a method of activating T lymphocytes for therapy for a subject/individual, wherein the method comprises producing the composition of silica particles by in situ synthesis prior to administration to the subject. As in other aspects of the present invention, activation of the T lymphocytes is generally characterised by an increase in expression of CD69 and/or CD25 by the T lymphocytes.

Alternatively or additionally, the present invention provides a composition for use in a method of T cell therapy which comprises obtaining a sample comprising T cells from a subject, contacting the T cell sample with the silica composition of the present invention to cause T cells in the sample to activate and administering (i.e. returning) the activated T cells to the subject.

As a further embodiment to the present invention, the inventors discovered that minimally toxic uSANS can be produced through an in situ synthesis, i.e. uSANS that are produced almost immediately before clinical application by either a batch synthesis or a flow synthesis approach. These in situ uSANS can be produced by a batch synthesis in quasi-neutral buffered systems. The in situ synthesis comprises a two solution system: (i) a silicate solution at pH>10.5 (i.e. silicate is soluble rather than colloidal) which is neutralised by a (ii) acidic buffer solution (comprising a carboxylate such as citrate or an amino acid such as glycine). Mixing the two solutions, results in a moderately acid pH 4.0 and 6.5 (and more preferably between pH 5.0 and 6.0) and cluster/colloidal silicates (i.e. nanosilica) are then rapidly formed. These colloids become gradually more condensed and can then be administered at a chosen point of lability. Preferably incubation will be carried out between pH 4.0 and 6.5 for slow incubations (batch in situ synthesis) or between pH 6.5 and 8.5 for fast incubations (flow in situ syntheses). The concentration of silicate during incubation preferably ranges between 10 and 100 mM, preferably between 20 and 60 mM. Incubation time are preferably between 15 and 60 min for in situ batch syntheses or between 10 seconds and 5 min for in situ flow syntheses (i.e. length of time between point of mixing and intravenous introduction). For example, 30 min incubation upon mixing the acid and the silicate components, will be appropriate for a batch synthesis at (i) 40 mM Si, (ii) room temperature, (iii) pH 5.3 (measured as pH 4.0-5.0 with pH strips). Additionally, for illustrative purposes, a flow synthesis may only require 1 minute incubation (within the reaction tubing), at room temperature and may comprise 50 mM Si (upon mixing the two components) at pH 7.0-8.0. Usefully, the present inventors discovered that the synthetic conditions can be fine-tuned for optimum particle lability through the use of a molybdate assay described herein (lability assay).

As a further embodiment to the present invention, in situ uSANS can be produced through a flow system. This is advantageous because the flow system can be linked to an intravenous delivery system, or a cell isolation/treatment system, thus minimising handling (and potential for contamination) between synthesis and delivery. In this flow synthesis two solutions are mixed in line: (i) a silicate solution at pH>10.5 (i.e. soluble silicate rather than colloidal) and ii) an acidic solution. Upon combining the two flows, a near neutral pH (pH 6.5-8.0) is achieved which results in the rapid formation of labile silicates that can be directly administered to a subject or a subject's cells extra corporeally. Usefully, this flow synthesis system is highly tuneable. For example, more condensed particles (if required) can be produced by employing longer reaction tubing, resulting in longer incubation times (in the reaction tubing) prior to injection to a subject or a device.

Figure 11:
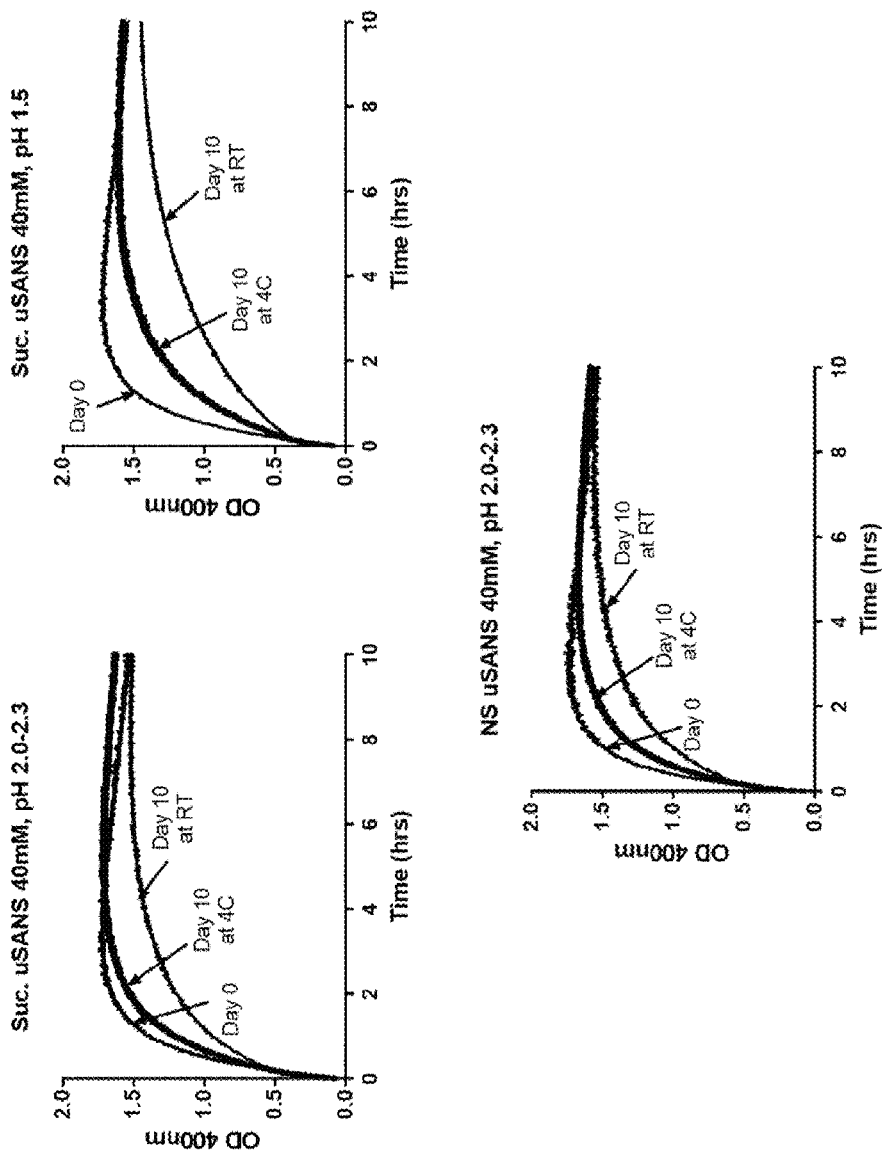
FIG. 11. Chemical lability of uSANS during acidic storage as determined by a molybdate assay. All materials were stored at room temperature or at 4° C. Sucrose-stabilised uSANS (Suc uSANS) were stored at pH 2.15±0.15 or 1.5±0.1, whereas non-stabilised materials (NS uSANS) were stored at pH 1.5±0.1. Higher ODs indicate greater chemical lability (i.e. less condensed silicates).
Figure 12:
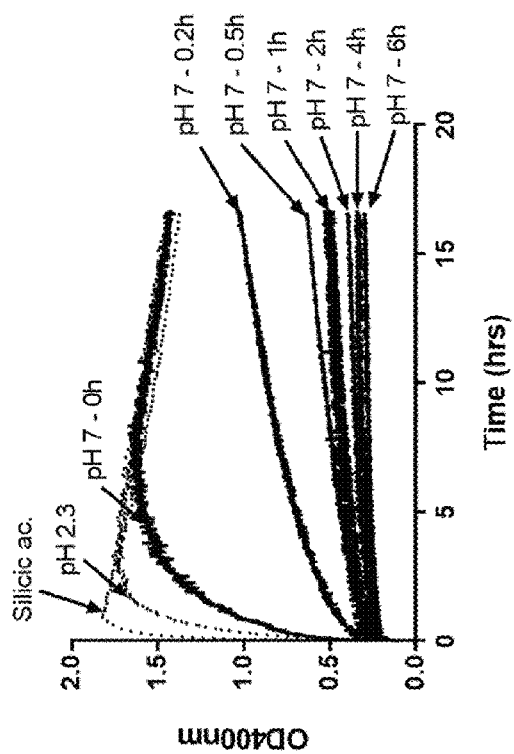
FIG. 12. Chemical lability of uSANS over time upon neutralisation (pH 7). A molybdate assay was used to compare the lability of soluble silicates (Si(OH)4) with uSANS prior to (pH 2.3) and after neutralisation (t 0 h to t 6 h).
Figure 13:
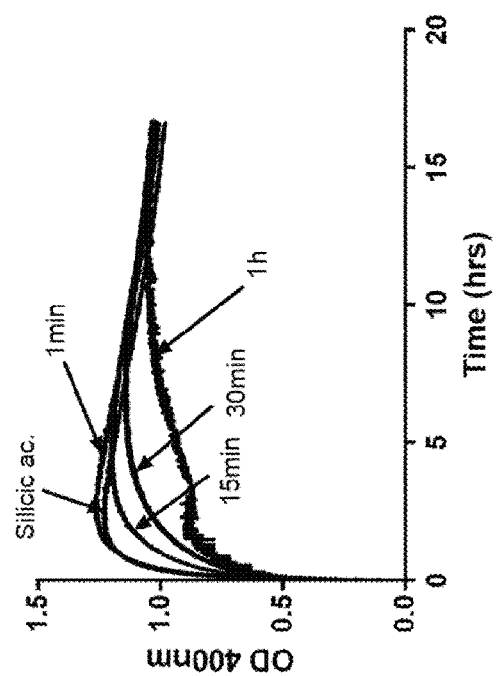
FIG. 13. Chemical lability of in situ formed uSANS (40 mM Si) after various incubation periods (1 min to 1 h).

Usefully, in situ uSANS are as effective at activating T-cells as the best standard uSANS but are less toxic. In particular, over short periods of exposure—representative of intravenous delivery where there is a rapid dilution of the active, in situ uSANS exhibit a complete lack of toxicity even at the highest concentration tested (4 mM; FIG. 9). These particles need to be persistently present with the endothelial cells to cause damage which would not occur in treatment protocols. A further advantage of the in situ uSANS system is that the shelf life of its component solutions is virtually 'infinite' since both buffer (e.g. citrate) and silicate solutions are extremely stable. This is in contrast with standard uSANS which become gradually less labile, as can be demonstrated by a molybdate assay, despite being stabilised by the low storage pH and, optionally, the presence of stabilising agents (FIG. 11). A further limitation to standard uSANS is that, due to their low pH, these solutions must be neutralised prior to administration (e.g. i.v. delivery). However, upon neutralisation, lability rapidly declines, which is a clinically undesirable feature. Indeed this effect is measurable immediately after neutralisation and after 12 minutes the colloids are no longer clinically usable (FIG. 12).

Nanosilica Compositions

The present invention relates the compositions comprising nanosilica in the form silica particles having a mean diameter between 0.5 nm and 20 nm, optionally stabilised by one or more stabilising agents. The findings described in the present application show that the nanosilica compositions of the present invention may be used in methods of activating T cells, and hence provide therapy for a subject or individual, in particular in the treatment of cancer and infections as discussed in more detail below.

Alternatively, compositions comprising stabilised nanosilica compositions that include stabilising agents and processes for their production are described in WO 2015/121666 (Medical Research Council) which is incorporated by reference in its entirety. Examples of stabilising agents suitable for use with the nanosilica composition of the present invention include polyols, sugars and/or quarternary ammonium salts, such as choline and carnitine. In particular, WO 2015/121666 provides processes for producing a stabilised polymeric silicate composition comprising polymeric silicic acid and nanosilica particles, in which polymerisation of silicates and particle size growth is controlled and the resulting particles are rendered size stable through the combination of silicate concentration, pH and/or stabiliser. In some embodiments, the compositions may additionally be doped with metal cations as these may induce particle size growth and may provide the compositions with useful additional properties.

The nanosilica compositions of the present invention comprise soluble polysilicic acid and nanosilica particles having mean diameters of 20 nm or less, and in some cases mean diameters that are more preferably less than 10 nm, more preferably less than 5 nm, 4 nm, 3 nm, 2 nm, 1 nm or 0.5 nm. In some embodiments, the particles may range from about 0.5 nm to about 2 nm, or from about 0.5 nm to about 3 nm, or from about 0.5 nm to about 4 nm, or from about 0.5 nm to about 5 nm, or from about 0.5 nm to about 10 nm, or from about 0.5 nm to about 15 nm, or from about 0.5 nm to about 20 nm, or from about 5 nm to about 20 nm, or from about 5 nm to about 15 nm, or from about 5 nm to about 10 nm, or from about 10 nm to about 15 nm, or from about 10 nm to about 20 nm, or from about 15 nm to about 20 nm. Preferred compositions include silica particles having a mean diameter between 0.5 and 10 nm and silica particles having a mean diameter between 2 and 5 nm.

The non-soluble nature of the polymeric silicic acid and/or nanosilica particles may be confirmed indirectly by the molybdic acid assay mentioned above as this determines the soluble silicic acid fraction. In general, the materials will be in equilibrium with the soluble silicic acid, with typical soluble silicic acid concentration being about <2 mM at pH<9.0. The nanosilica compositions of the present invention may be contrasted with more condensed forms of silicates, including larger nanoparticles (e.g. preferably having an average size greater than 50 nm, and more preferably greater than 20 nm), polysilicic acid gels and silicon dioxide ($SiO_2$) the fully condensed form of silicic acid, in which —OH groups are virtually absent. The size of the particles of polysilicic acids can be determined using dynamic light scattering and it is preferred that the measurements are made on freshly prepared samples, if not stabilised. As will be understood by those skilled in the art, the polysilicic acids will be in equilibrium with other silicate species. For example, and depending on the precise conditions present, this may include smaller amounts of soluble silicic acid.

The compositions of nanosilica particles used in the present invention are generally aquated, that is water is present throughout their synthesis and, at least to some degree (e.g. at least 5 wt %, more preferably at least 10 wt %, at least 20 wt % water), preferably also in the final formulation, i.e. the materials are not dried or significantly heated prior to formulation and subsequent administration. It will be clear, however, that stabilisers or other formulation agents may be used at such a high concentrations that displaces water molecules from the silicate particles. As such, the water may be displaced although the formulation is not dried.

The stabilisation of the compositions nanosilica particles used in accordance with the present invention preferably extends from their synthesis to their storage, formulation and/or administration (e.g. unwanted lack of agglomeration).

The compositions nanosilica particles used in accordance with the present invention are metastable, that is the compositions possess a stability that is fit for the purpose of shelf-life of their intended use. By way of illustration, it is preferred that the polymeric silicate compositions of the present invention are storage stable, for example being stable for 3 months or more, more preferably for 6 months or more, more preferably for 12 months or more, and more preferably 24 months or more. Thus, the polymeric silicate compositions of the present invention may be produced by partial condensation of silicic acid (or silicate) molecules. These materials are metastable as discrete, non-aggregated clusters or colloids.

In some embodiments of the present invention, the compositions of nanosilica particles include a stabilising agent, preferably a sugar and/or a polyalkylene glycol. The sugars include oligosaccharides composed of eight monosaccharides or fewer, such as monomeric, dimeric or trimeric saccharides. A preferred sugar is sucrose. The maximum number of monomeric units in the sugar is chosen such that its administration does not elicit an immune response in the subject on administration. Polyalkylene glycols are a family of polyether compounds that include polyethylene glycol (PEG) and polypropylene glycol. Examples of stabilising agents that are sugars (saccharides) include monomeric, dimeric, trimeric and polymeric sugars (saccharide), or the corresponding sugar alcohols, such as glucose, fructose, mannose, sucrose, threitol, erythritol, sorbitol, mannitol, galactitol or adonitol. In some embodiments in which the stabilising agent is a sugar, it is an oligosaccharide other than lactose. In some embodiments in which a sugar alcohol is used, it is other than mannitol. The use of sugars as stabilising agents for compositions that are administered internally is preferred in the present invention as they are safe for administration to human and animal subjects.

In some embodiments, it is possible to employ combinations of more than one different sugar(s) or polyalkylene glycol(s), e.g. two, three, four or five or more sugars or polyalkylene glycols, e.g. by adding them in step (a) and/or (b). Sugar and/or polyalkylene glycol stabilising agents are generally added at a concentration between 0.01 M and 3.0 M, and more preferably between 0.03 and 2.0 M, and most preferably between 0.1 M and 1.5 M. The skilled person can carry out routine tests to determine which combinations of sugars and/or polyalkylene glycols work best in any given situation.

The stabilised nanosilica compositions of the present invention may be distinguished from the compositions disclosed in US Patent Publication No: 2003/0206967 (Choi et al.) which describe a composition that comprises sodium metasilicate, borax, sodium thiosulfate, potassium carbonate and refined sugar in water. This results in a very alkaline composition having a pH of about pH 13, in contrast to pHs of the stabilised polymeric silicate compositions of the present invention, which are preferably between pH 3.0 and 9.0, more preferably between 3.0 and 8.0 and more preferably between 5.5 and 7.5. The process used to make the compositions of Choi et al. differs from the present invention as the present invention produces the compositions by lowering the pH to produce stable silicate polymers. In view of the above, it is preferred that the nanosilica compositions used in the present invention do not comprise one or more of sodium metasilicate, borax, sodium thiosulfate, potassium carbonate, and preferably do not include borax. Preferred nanosilica compositions of the present invention may be choline free and/or ethanol free, and hence differ from Biosil™ and the silicates compositions described in Kerek respectively.

In other aspects, the present invention may use carboxylic acids as stabilizing agents and the carboxylic acid may be a $C_{2-10}$ carboxylic acid, for example a dicarboxylic acid such as oxalic acid, malonic acid, glutaric acid, tartaric acid, succinic acid, adipic acid or pimelic acid, or ionised forms thereof (i.e., the corresponding carboxylate), such as adipate. Or for example a monocarboxylic acid, such as gluconic acid. Further examples of stabilizing agents are dicarboxylic acids, which may be represented by the formula HOOC—$R_1$—COOH (or an ionised form thereof), where $R_1$ is an optionally substituted $C_{1-10}$ alkyl, $C_{1-10}$ alkenyl or $C_{1-10}$ alkynyl group. In general, the use of carboxylic acids in which $R_1$ is a $C_{1-10}$ alkyl group, and more preferably is a $C_{2-6}$ alkyl group, is preferred.

The present inventors also surprisingly found that nanosilica compositions of the present invention may be further stabilised by adding a non-aqueous solvent, such as an alcohol. A preferred example of an alcohol is ethanol. By way of illustration, the non-aqueous solvent may be added between 10 and 50% v/v, or between 20 and 50% v/v or between 10 and 20% v/v. Furthermore, in some cases the present inventors found that the combination of sucrose with alcohol was particularly effective for stabilising the nanosilica compositions.

In the following discussion of the steps of the processes of the present invention, it will be apparent to those skilled in the art that it may be possible to reorder some of the steps of the above process and/or for some of the steps to take place simultaneously. Others of the steps are optional as indicated above and explained further below.

In the work leading to the present invention, the inventors found that a number of factors contribute to the stability of the nanosilica compositions including the rate at which the pH of the starting alkaline silicate solution is lowered, the inclusion of stabilisers, notably sugars or polyalkylene glycols, the addition of metal cations and/or the addition of a non-aqueous solvent. The processes for producing nanosilica compositions may employ these approaches, alone or in any combination, to produce nanosilica compositions having sufficient stability for use, e.g. as supplements or therapeutic agents.

In some cases, in particular for the production of ultra small particles of nanosilicates ("uSANS"), the rate at which the pH of the alkaline silicate solution is lowered may have a significant effect on the stability of the resulting nanosilica compositions. Preferably, the pH is lowered (e.g. to a pH of less than or equal to pH 4.0 or 3.0) over a period of less than 60 seconds, more preferably less than 30 seconds, more preferably less that 10 seconds, or most preferably less that 5 seconds. The production of an alternative silica particle composition HS-7 is provided in the examples below.

It is preferred that the concentration of the alkaline silicate solution is between 0.05 M and 1.5 M, and more preferably is between 0.03 and 2.0 M, and most preferably between 0.1 M and 1.0 M. The use of pHs that are higher than 9.5 is also preferred in order to maintain the solubility of the silicates, and preferably in step(a) the pH of the alkaline silicate solution is about pH 10.5 or above, and still more preferably is about pH 11.5 or above. In the final polymeric silicate compositions, the concentration of silicon may be 2.5 mM or more, 5.0 mM or more, 25 mM or more, 30 mM or more, 40 mM or more, 50 mM or more, 100 mM or more, 250 mM or more, 500 mM or more. In the final stabilised polymeric silicate compositions, the concentration of silicon may be 1.5M or less, 1.0M or less, 500 mM or less, and ranges between these lower and upper limits.

In some embodiments, the reduced pH may have an effect on the type of stabilised silicate nanoparticles that can be produced. As shown in the examples, uSANS or very small particles that have mean diameters of 5 nm or less can be formed by rapidly dropping the pH from pH greater than 10 to 3.0 or less and enable concentrations of silicon up to 1 M to be used. Alternatively, SANS or small nanoparticles have mean diameters of 10 nm of less and may be formed by reducing the pH to about 7.4. In this case, lower concentrations of about 50 mM or less can be used. Accordingly, the reduced pH may be 7.4 or lower, or pH 3.0 or lower. This enables the preparation of uSANS at a low pH, as described, the pH raised to grow uSANS to SANS of a determined particle size, and the size stabilised by dropping the pH again, should this be required. Optionally, stabiliser is required at some stage in this process. These processes are an important part of the art.

In some case, the pH may be lowered and/or the suspension diluted for long term storage of stabilised aqueous suspensions. Alternatively or additionally, upon long term storage at a non-physiological pH and prior to administration to a subject, the nanosilicate suspension may be adjusted to a physiological pH, and/or diluted and/or stabiliser added.

The composition may be stabilised, such that the particle size of the nanosilicates will remain sufficiently stable (<20 nm) for the intended application. For example, in the case of a formulation for intravenous administration, the particle size of the first storage solution (e.g. at pH<3 and 100 mM Si) will be stable for the duration of the storage period and then once diluted with a buffered i.v. solution it will remain stable first for the few hours before application and then, once administered, it will not undergo agglomeration.

Synthetic Methodology for Batch Synthesis of In Situ uSANS (Citrate)

Preparation of Stock Solutions

Component A (HCl+Citric acid): (i) Dissolve 0.307 g of citric acid (MW 192.124) in 180 ml of UHP water; (ii) Add 0.783 ml of 37% HCl under agitation; (iii) Adjust the volume to 200 ml with UHP water.

Component B (80 mM Sodium silicate): Dilute 2.56 ml of sodium silicate (~6.25M Si) in a final volume of 200 mL water Component C (saline; optional): 4.5 g of NaCl are dissolved in 45 ml of UHP water and the final volume adjusted to 50 ml with UHP water.

Sterilisation of components A, B and C (optional):Under sterile conditions (flow cabinet), syringe filter the component solutions through a 0.22 μm filter into a sterile container.

Preparation of Colloids

Step 1: Component A (2.5 mL) is mixed with component B (2.5 mL). The resulting pH is circa 5.4 as measured by a pH electrode (pH strips 4.0-5.0).

Step 2: Incubate for 30 min

Step 3 (optional): After incubation and immediately prior to administration, component C (0.425 mL) is added and mixed.

Synthetic Methodology for In Line Synthesis of In Situ uSANS (Unbuffered)

Preparation of Stock Solutions

Component A (HCl): Dilute 1.2 ml of 37% HCl in final volume of 100 mL water.

Figure 6:
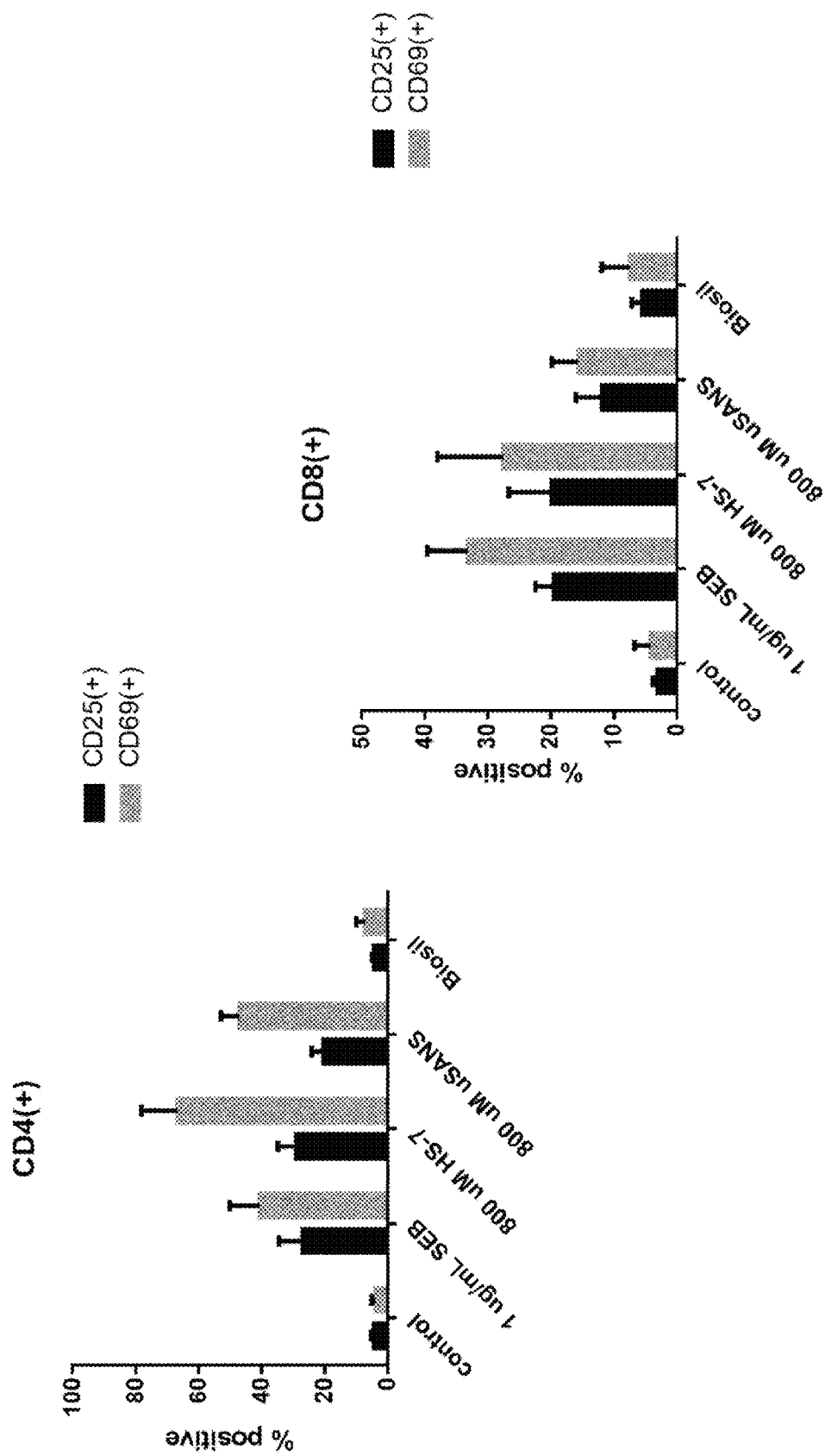
FIG. 6. CD4+ and CD8+ expression by silica particle compositions of the present invention compared to Biosil™ (+positive control, SEB).
Figure 7:
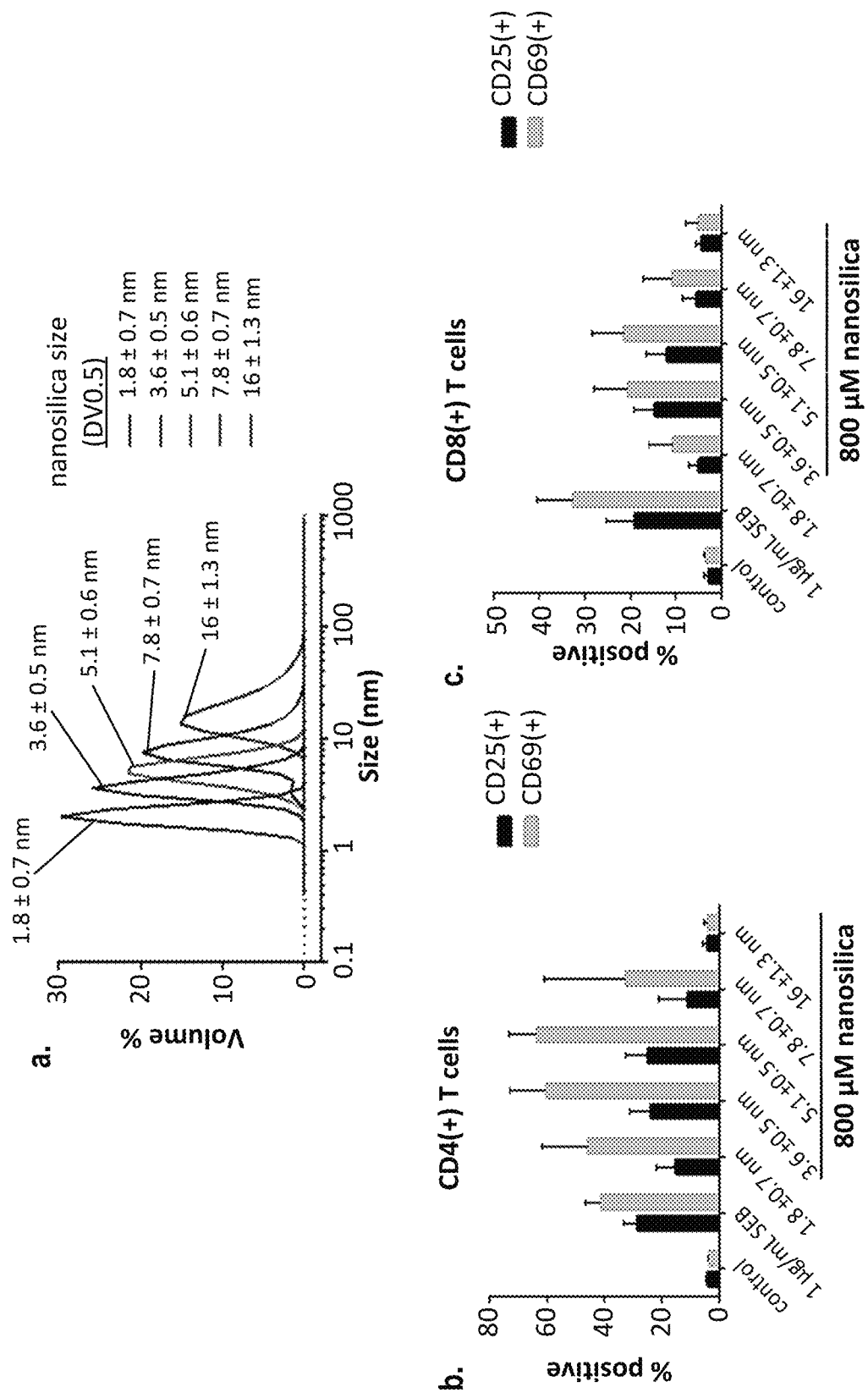
FIG. 7. The activation of CD4 and CD8 T cells by ultrafine nanosilica of differing size, prepared by pH neutralisation (pH 7) of an alkaline sodium silicate solution to a final concentration of 23-40 mM Si±sodium chloride and incubation for ~20 h (for dispersions>3 nm) or by adjusting a 500 mM alkaline silicate solution to pH 0.8-1 and incubating for ~20 h (<3 nm dispersions) prior to addition to cell cultures (n=>8). Particle mean diameters (DV 0.5) are reported.

Component B (50 mM Sodium silicate): Dilute 0.8 mL of sodium silicate (Sigma-338443, ~6.25M Si) in a final volume of 100 mL water Preparation of Colloids Colloids are prepared in flow system as represented in FIG. 6 using a reaction tubing with a length of 30 cm. Syringe pump A and B were operating at 1.05 and 48.5 mL/h, respectively, which resulted in a pH of 7.55.

Formulation and Uses of Compositions

The nanosilica compositions of the present invention may be formulated for use in as silicate-containing therapeutic agents. The compositions may comprise, in addition to the nanosilica particles, a pharmaceutically acceptable excipient, carrier, buffer, stabiliser or other materials well known to those skilled in the art. Such materials should be non-toxic and should not interfere with the efficacy of the nanosilica particle compositions.

The experiments described herein demonstrate that the nanosilica particle compositions of the present invention are capable of directly activating T lymphocytes as determined by an increase in expression of the biomarkers CD69 and/or CD25, for example as compared to an untreated control sample of T lymphocytes. The assays and methods of the present invention may be used in the screening and development of effective therapeutic silica particle compositions, and for determining the effectiveness of therapies administered to a subject or individual.

The activation of T lymphocytes using the present invention may be used in the treatment of a range of conditions or disorders where this would have therapeutic benefit to a subject, whether this is by way of treatment or prophylaxis, and with the advantage that, when administered at an appropriate concentration, the silica particle compositions used in the present invention are not substantially directly cytotoxic to cancer cells. Cancers may also include but are not restricted to: melanoma, skin cancers, lung cancer, pancreatic cancer, colon rectal and other splanchnic cancers, gastric cancer, breast cancer, lymphomas, leukaemias, uterine cancers, prostate cancer, oesophageal cancer, bone cancers, bladder cancers, cervical cancer, endometrial cancer, brain cancer, eye cancers, ovarian cancer, testicular cancer, liver cancer, renal cancer, head and neck cancers and includes metastatic and primary cancers.

However, while one preferred use of the present invention in in the treatment of cancer, the T cell therapies described herein may be used for the treatment of other conditions, in particular the treatment of infection, such as bacterial infection or viral infection. Infection includes, but is not limited to: infection with viruses, retroviruses and bacteria such as Mycobacteria, Gram positive bacteria and Gram negative bacteria, as well as helminths, parasites and other infectious agents. The transiently stable silicate nanoparticles may also act as a reservoir for the release of silicic acid that itself is effective in enhancing connective tissue health and may be useful in osteoporosis, fracture healing, joint diseases, skin diseases, blood vessel disorders.

As such, administration may be by parenteral administration, the latter especially by intravenous administration.

Other medical uses of the compositions of the present invention include the treatment of hypertension, diabetes, bone diseases, cardiovascular diseases, neurodegenerative pathologies, cancer of all types not noted above, hyperacidity, osteoporosis, dental calculus, Alzheimer disease, Creutzfeld-Jacob disease as well as for wound healing. Other medical uses of the compositions of the present invention include the treatment of skin affected by burn, wounding or action of pathogens or of caustic chemicals, including the treatment of sun burn, or any skin disease including psoriasis, eczema and dermatitis of other sorts.

In some aspects, medical uses of the present invention using activated T lymphocytes are for use in the treatment of a human subject. However, as well as having applications for the treatment or prevention of conditions in human subjects, the present invention has application in the veterinary field, for example for use in the treatment of a non-human animal, and more especially non-human mammals such as dogs, cats and horses.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the silicate-containing supplement needs to be maintained in a solid form, e.g. to control the delivery of a component of the material, it may be necessary to select components of the formulation accordingly, e.g. where a liquid formulation of the material is made. Preservatives, stabilisers, buffers, antioxidants and/or other additives may be included, as required, for example in embodiments of the present invention in which the polymeric silicate compositions are suitable for administration to a subject via a drip.

In therapeutic applications, nanosilica compositions used in accordance with the present invention are preferably given to an individual in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc. is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

Materials and Methods

Preparation of Silica Particle Composition HS-7

HS-7 was prepared by diluting 0.1 g sodium silicate (cat. #338443; Sigma-Aldrich Chemical Co., Gillingham, UK) in 20 g distilled deionized water (DDW; 18 MΩ/cm) and adjusting to pH 6.7-7.0 (pH test stripes, Sigma-Aldrich Co., cat. # P3536) with hydrochloric acid (HCl, 4-5 M). The dispersions were left to equilibrate for 16-24 at room temperature.

Preparation of Silica Particle Composition "uSANS"

Ultra-small amorphous nanosilica (uSANS) nanoparticle dispersions (1.9 nm) were prepared according to WO 2015/121666. uSANS was prepared by diluting 4 mL sodium silicate (cat. #338443; Sigma-Aldrich Chemical Co., Gillingham, UK) in 30 mL distilled deionized water (DDW; 18 MΩ/cm). 2 mL HCl (37%) was added rapidly while mixing. The solution was diluted to 50 mL with H2O and incubated at room temperature 16-24 h prior to use.

Comparative Silica Compositions According to Example 4 of US 2011/0229577 (Kerek)

7.4 ml of TMOS were mixed with 25 ml of UHP water. The pH was adjusted to 3.6 with acetic acid (0.5M) and the resulting mixture was incubated for 5 minutes at 45 C in an oil bath under stirring. Next, the suspension was let cool down at room temperature for 40 minutes and pH adjusted to 2.0 with 1M HCl. Finally, methanol was removed using a rotavapor (T=40-45 C).

Cellular Assays

Peripheral blood mononuclear cells (PBMC) were isolated from single leukocyte cones purchased from the National Blood Service (Cambridge, UK) using density gradient centrifugation. Cells were froze down in freezing media (10% DMSO, 50% FBS, 40% RPMI 1640). Frozen cells were thawed, washed in RPMI, and rested 2 h in RPMI containing 10% FBS, 0.3 g/L L-glutamine, 1% penicillin-streptomycin and 0.01 µg/mL DNase. Cells were resuspended in RPMI+20% FCS to 2×106 cells/mL and 0.5 mL was added to FACS tubes followed by 0.5 mL RPMI+/− 1600 uM nanosilica treatment (giving 1.0×106 cells/mL, 800 uM nanosilica). Cells were incubated for 24 h, washed with PBS+1% BSA, and stained with FACS antibodies and a viability marker(CD3, CD4, CD8, CD25, CD69, 7-AAD viability marker). Cells were immediately analysed on a Cyan-ADP flow cytometer using Summit software for acquisition & analysis (Beckman Coulter), acquiring a minimum of 400,000 events per sample.

The Activation of CD4 and CD8 T Cells by Ultrafine Nanosilica

Peripheral blood mononuclear cells (PBMC) were isolated from single leukocyte cones purchased from the National Blood Service (Cambridge, UK) using density gradient centrifugation. Cells were frozen down in freezing media (10% DMSO, 50% FBS, 40% RPMI 1640). Frozen cells were thawed, washed in RPMI, and rested 2 h in RPMI containing 10% FBS, 0.3 g/L L-glutamine, 1% penicillin streptomycin and 0.01 µg/mL DNase. Cells were resuspended in RPMI+20% FCS to 2×106 cells/mL and 0.5 mL was added to FACS tubes followed by 0.5 mL RPMI+/− 1600 uM nanosilica treatment (giving 1.0×106 cells/mL, 800 uM nanosilica). Cells were incubated for 24 h, washed with PBS+1% BSA, and stained with FACS antibodies and a viability marker (CD3, CD4, CD8, CD25, CD69, 7-AAD viability marker). Cells were immediately analysed on a Cyan-ADP flow cytometer using Summit software for acquisition & analysis (Beckman Coulter), acquiring a minimum of 400,000 events per sample.

The Activation of Different Th Lineage Cell Types by Ultrafine Nanosilica

Peripheral blood mononuclear cells (PBMC) were isolated from single leukocyte cones purchased from the National Blood Service (Cambridge, UK) using density gradient centrifugation. Cells were frozen down in freezing media (10% DMSO, 50% FBS, 40% RPMI 1640). Frozen cells were thawed, washed in RPMI, and rested 2 h in RPMI containing 10% FBS, 0.3 g/L L-glutamine, 1% penicillin streptomycin and 0.01 µg/mL DNase. Cells were resuspended in RPMI+20% FCS to 2×106 cells/mL and 0.5 mL was added to FACS tubes followed by 0.5 mL RPMI+/−17 uL or 35 uL nanosilica treatment (giving 1.0×106 cells/mL, 400 and 800 uM nanosilica, respectively). Cells were incubated for 24 h, washed with PBS+1% BSA, and stained with FACS antibodies and a viability marker (CD3, CD4, CD8, CD25, CD69, CD40L, LAP, GARP, 7-AAD viability marker). For the intracellular staining of FoxP3, cell membranes were treated with a cell membrane permeabilisation buffer prior to intracellular staining. Cells were immediately analysed on a Cyan-ADP flow cytometer using Summit software for acquisition & analysis (Beckman Coulter), acquiring a minimum of 400,000 events per sample. For IFN gamma cytokine analysis, cell supernatants collected at the end of incubation were assayed for the presence of IFN gamma using standard ELISA kits according to the manufacturers' instructions.

Toxicity of Three Different Forms of Nanosilica on Endothelial Vein Cells

Human Umbilical Cord Vein Endothelial Cells (HUVEC; ATCC, Manassas, USA) were resuscitated from cryo-storage in liquid nitrogen and maintained in complete growth medium: F-12K Medium (ATCC), supplemented with 10% foetal bovine serum (FBS 'Gold'; PAA Laboratories, UK), 50 µg/mL penicillin and streptomycin (Invitrogen Ltd, Life Technologies UK), 0.1 mg/mL heparin (Sigma Aldrich Chemical Co, UK) and 0.05 mg/mL Endothelial Cell Growth Supplement (Alfa Aesar, UK). Cells were grown in Nunc T75 culture flasks (75 cm2; VWR International, UK) at 37° C. in a humidified atmosphere containing 5% CO2. For experiments, cells were detached at 70% confluence with 0.1% trypsin/0.02% EDTA solution and seeded into 48-well plates with 1 mL complete growth medium per well. Cells were grown to a confluent monolayer.

Nanosilica treatment. Three nanosilica preparations were tested. These are termed HS7, in situ uSANs and sucrose uSANs which, respectively, refer to nanosilica prepared in the following ways: Suc. uSANS: 1 day old uSANS was prepared by rapidly acidifying 500 mM Si(OH)4+1.5 M sucrose to pH 0.8-1 and immediately diluting to 40 mM with H2O+glucose (final glucose concentration 136 mM). The dispersion was incubated overnight and neutralized to pH 7 immediately prior to use.

In situ uSANS; (pH 5.0; batch synthesis; citrate buffered) was prepared by mixing 1 mL 80 mM Si(OH)4 and 1 mL citrate (8 mM, +47 mM HCl). The solution was incubated for 30 min and 0.17 mL 10× saline was added prior to use.

These were added to cells in the complete growth medium at final silicon concentrations of 1, 2 and 4 mM total Si. These treatments were compared with untreated cells and vehicle treated cells—the three vehicles (one per nanosilica preparation) were tested at the equivalent dose to the 4 mM nanosilica treatments. Each treatment and control was tested in sextuplicate (ie n=6). Briefly, the medium was aspirated from sextuplicate wells, the nanosilica was diluted in complete growth medium and immediately added to wells (0.5 ml per well).

Following addition of nanosilica or vehicle treatments to the cells, the 48 well plates were placed into the IncuCyte Zoom live cell imaging system (Essen BioScience Inc., USA) and phase-contrast images were acquired every 2 h, over a 68 h period.

pZap70 Induction in T Cells by Nanosilica

Peripheral blood mononuclear cells (PBMC) were isolated from single leukocyte cones purchased from the National Blood Service (Cambridge, UK) using density gradient centrifugation. Cells were frozen down in freezing media (10% DMSO, 50% FBS, 40% RPMI 1640). Frozen cells were thawed, washed in RPMI, and rested 2 h in RPMI containing 10% FBS, 0.3 g/L L-glutamine, 1% penicillin streptomycin and 0.01 µg/mL DNase. T cells were enriched using untouched Pan T cell isolation kits. Cells were resuspended in RPMI+20% FCS to 2×106 cells/mL and 0.5 mL was added to FACS tubes followed by 0.5 mL RPMI+/− 1600 uM nanosilica treatment (giving 1.0×106 cells/mL, 800 uM nanosilica). Cells were incubated for 0-6 h, spun down and lysed using NuPage LDS sample buffer. Western Blot analysis was conducted on the lysates, staining for vinculin (internal control, (An et al., 2012; Solan et al., 2003)) and pZap70 (Tyr319). The band intensities were quantified through integration and represented as a percentage of the internal control.

After the TCR/CD3 complex is engaged by a pMHC complex, superantigen or mitogenic antibody, T cell activation is initiated through the phosphorylation of the zeta-chain associated protein kinase 70 (Zap70), located on the phosphorylated immunoreceptor tyrosine-based activation motifs (ITAM) (Love and Hayes, 2010). Phosphorylated Zap70 (pZap70) then phosphorylates downstream proteins leading to signalling through nuclear factor of activated T cells (NFAT) and an activated T cell response (Chakraborty and Weiss, 2014; Fathman and Lineberry, 2007; Rossy et al., 2012; Wang et al., 2010).

Molybdate Dissolution Assay

A molybdate dissolution assay involves taking a sample of a polymeric silicate composition and diluting it in buffer. A molybdic acid assay may be used to determine the concentration of soluble silicate present in an aliquot of the buffer over time course of the assay. As shown in the examples, the composition may be diluted in 50 mM HEPES buffer and at pH 7.0-7.4. An exemplary molybdic acid assay employs 100 µL of the test solution or standard (prepared from Sigma Aldrich Si ICP 30 standard, 1000 mg/L) and 200 µL molybdic acid colouring solution (34.5 mM Mo (added as $NH_4Mo_7 \cdot 4H_2O$) and 0.15 M $H_2SO_4$). The assay solution is transferred to a well plate and mixed for 10 minutes. After the incubation, the absorbance (400 nm) can be measured and the concentration of soluble silicic acid determined using a standard curve.

Molybdate Lability Assay 7.5 µl of 40 mM Si suspensions were transferred to a 96 well plate and very quickly 100 µL of UHP water followed by 200 μL of molybdic acid solution (34.5 mM NH4Mo7O244H2O in 0.15 M H2SO4) were added. The absorbance at 400 nm was measured every 60 s for 17 h. A solution of 40 mM Silicic acid was used as a control in the assay.

Dissolution Assay

Whole blood was collected in heparin tubes and briefly mixed. Further heparin was added (to a concentration of 0.5 mg/mL) to prevent coagulation. nanosilica and successively diluted according to the following schedule, 16 mM for 25 s, 4 mM for 1 h, 2 mM for 3 h and 1 mM for 20 h. After treatment and incubation, the red blood cells were lysed, stained and FACS was conducted immediately. For the positive control, SEB was added to whole blood at 2 ug/mL. This assay showed that in situ uSANS (citrate buffered, batch synthesis) had the same stimulatory profile as standard uSANS as determined by CD4(+)–CD25, CD4(+)–CD69, CD8(+)–CD25, and CD8(+)–CD69 readouts.

Results

Figure 2:
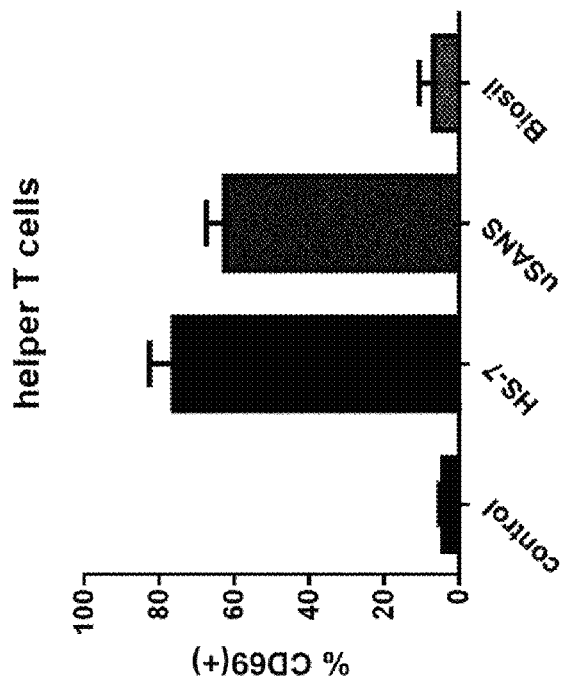
FIG. 2. T cell activation by silica particle compositions of the present invention and ch-OSA® (choline-stabilized orthosilicic acid, BioSil™)
Figure 2:
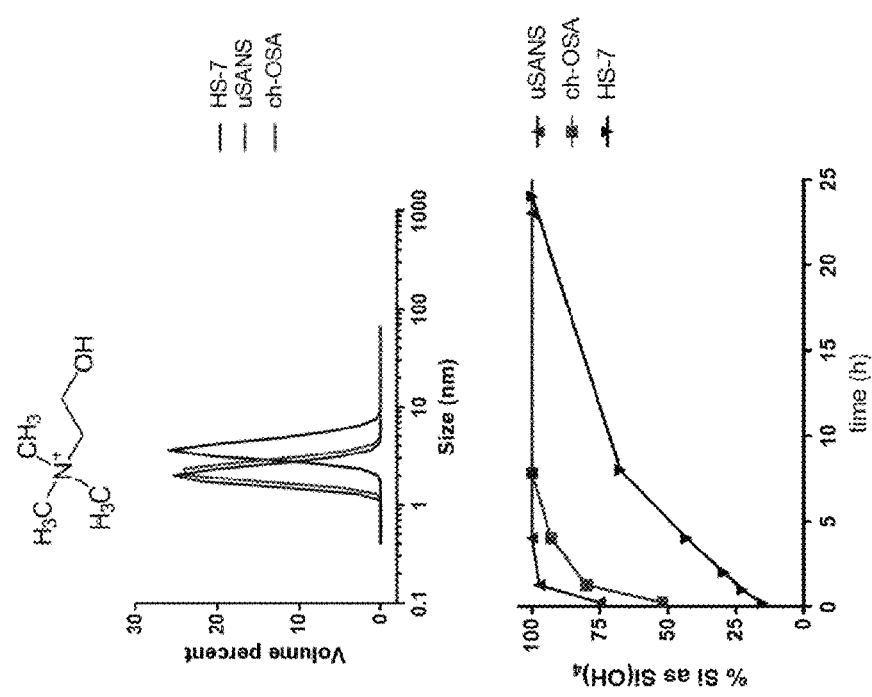
Figure 3:
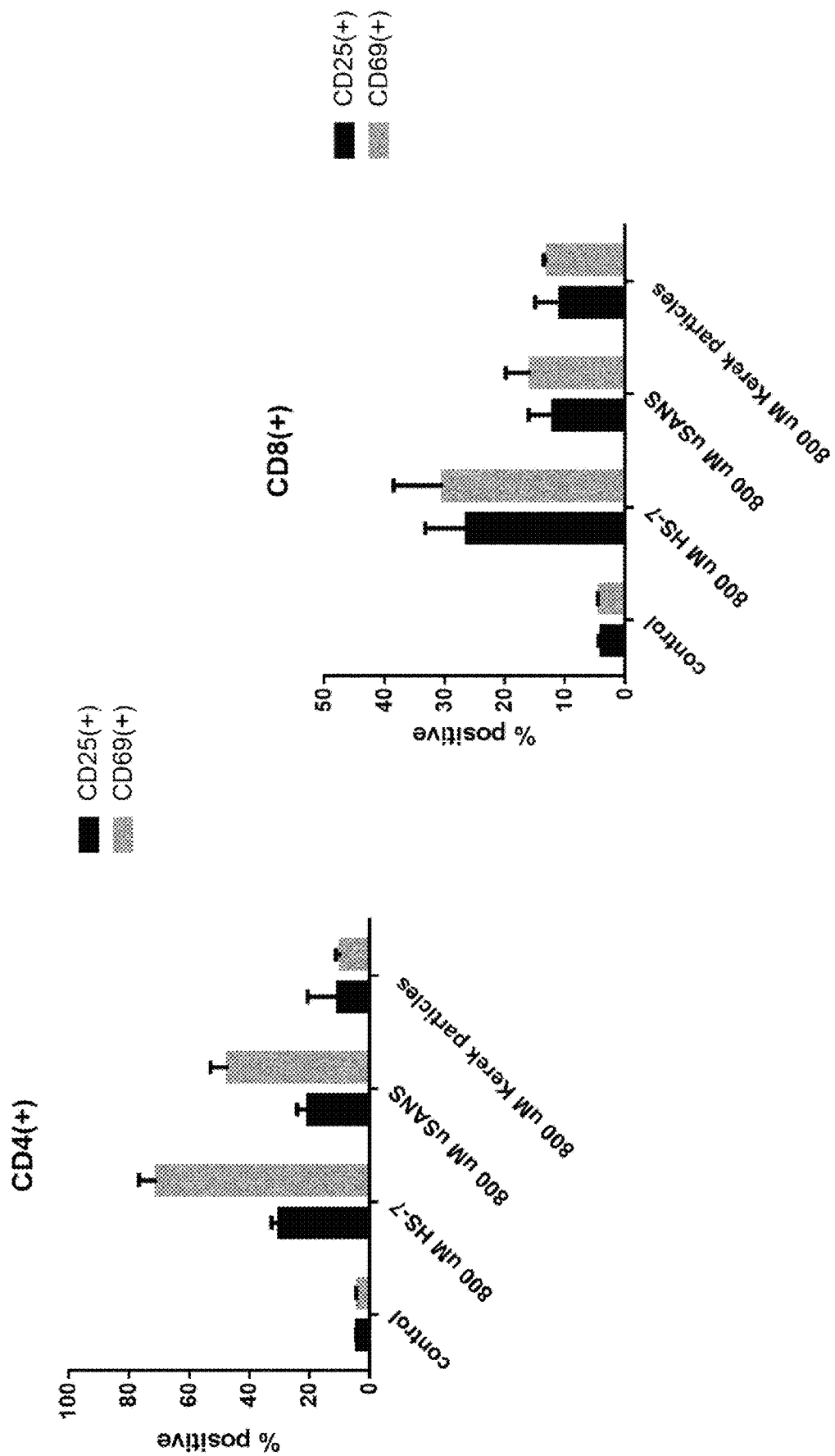
FIG. 3. CD4+ and CD8+ expression by silica particle compositions of the present invention compared to Kerek.
Figure 4:
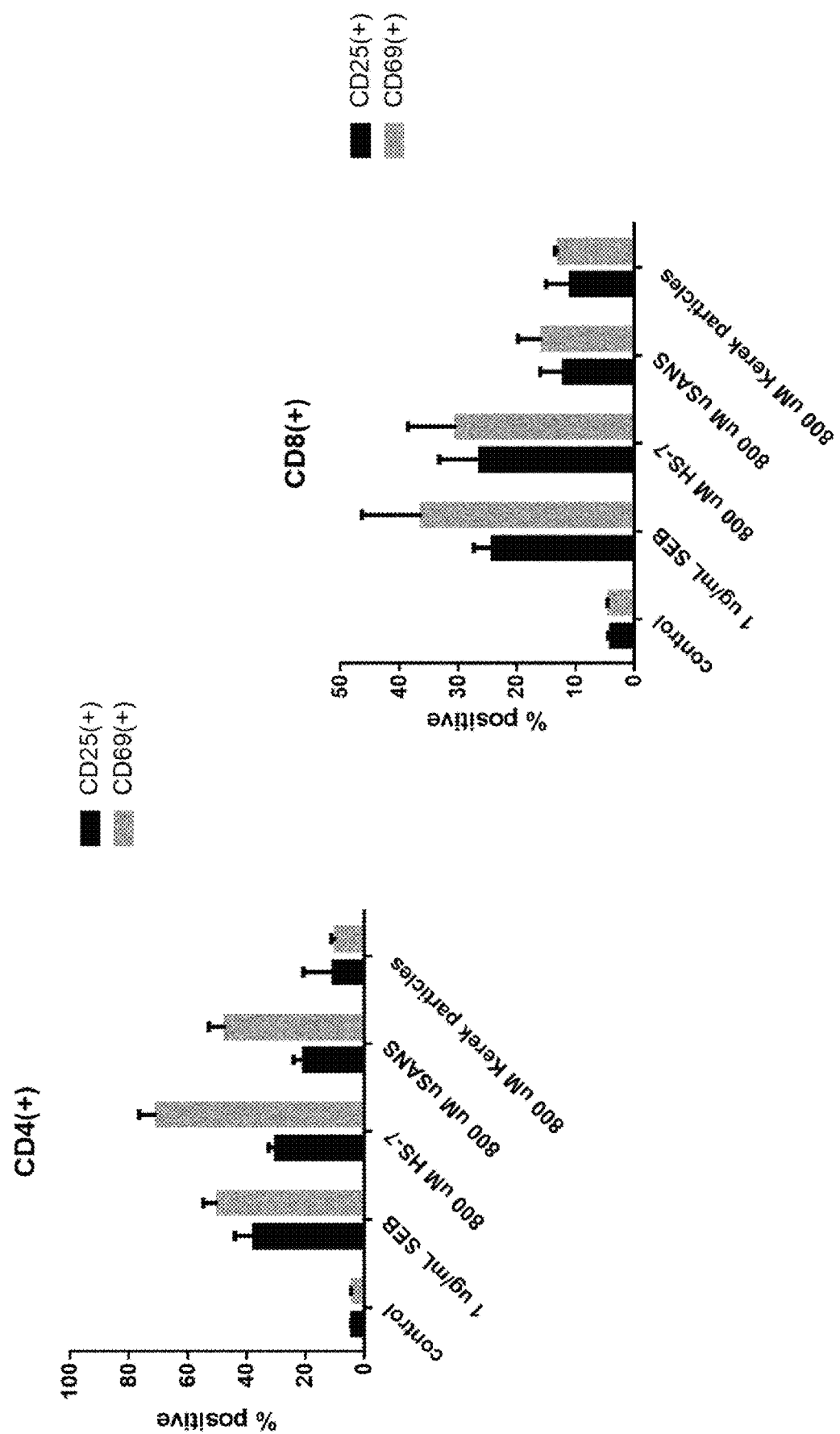
FIG. 4. CD4+ and CD8+ expression by silica particle compositions of the present invention compared to Kerek (+positive control, SEB).
Figure 5:
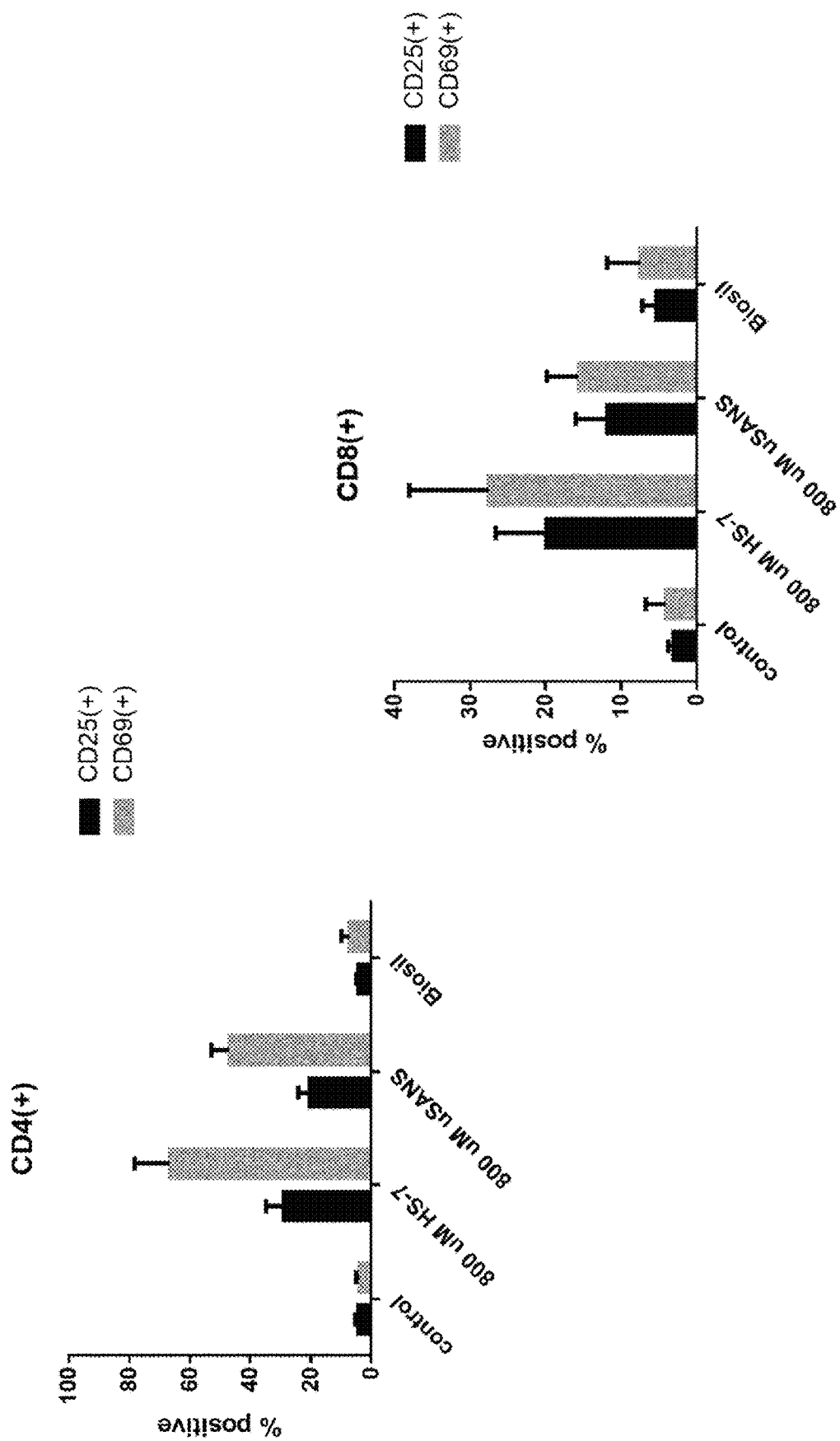
FIG. 5. CD4+ and CD8+ expression by silica particle compositions of the present invention compared to Biosil™.

The experiments described above demonstrate that only ultrafine nanosilica induces chronic activation of T lymphocyte cells (neither soluble silicic acid ($Si(OH)_4$ nor larger silica particles (e.g. >10 nm) do this). FIGS. 1 and 2 show the expression of the activation marker CD69 on helper T cells after silicic acid and ultrafine nanosilica treatment for 24 h, compared to an unstimulated baseline control and the silicates produced according to US 2011/0229577 (Kerek, FIG. 1) and the commercially available choline stabilised orthosilicic acid composition, Biosil™ (FIG. 2). FIGS. 3 to 6 show similar comparisons, with the addition that the T lymphocyte superantigen SEB (*Staphylococcal enterotoxin B*) was used a positive control. The silica particle compositions of the present invention were show to induce T cell activation by increasing CD25 and CD69 activation marker expression levels. Again, silicic acid had no effect on the expression of the activation markers on T cells (data not shown). Ultrafine nanosilica of the present invention also induced chronic activation of the T cells, comparable to that of the superantigen SEB. The figures show that nanosilica activates both T helper (CD4+) and cytotoxic (CD8+) T cells (i.e., that they become CD25 and CD69 positive upon nanosilicate exposure).

The experiments described herein show that T cells of multiple lineage types may be susceptible to T cell activation via these ultrafine nanosilica particles (FIG. 8).

However, despite being better tolerated than HS7 particles, uSANS particles still exhibit moderate toxicity to endothelial cells (FIG. 9). However, minimally toxic uSANS can be produced through an in situ synthesis. This can either be a batch synthesis in quasi-neutral buffered systems or alternatively through a flow synthesis. These results may also be replicated with uSANS produced using an in situ synthesis method as described herein.

REFERENCES

All documents mentioned in this specification are incorporated herein by reference in their entirety.

Jugdaohsingh et al., Is there a biochemical role for silicon?, in Metal Ions in Biology and Medicine, Volume 10, pages 45-55, 2008, John Libbey Eurotext: Montrouge.
WO 2009/052090.
US Patent Publication No: 2009/0130230.
US Patent Publication No: 2013/0149396.
U.S. Pat. No. 5,807,951 (Nippon Zoki Pharmaceutical Co., Ltd.)
WO 95/21124.
EP 1 371 289 A.
US Patent Publication No: 2011/0229577 (Kerek).
Kim et al. (Macromolecules, 45: 4225-4237, 2012).
Gao et al (Colloids and Surfaces A: Physicochem. Eng. Aspects 350: 33-37, 2009).
Jaganathan H, Godin B. *Biocompatibility assessment of Si-based nano-and micro-particles*. Adv Drug Deliv Rev. 2012 May 22.
Kerek, F. Biologically active silicic acid. EP2 151 466 A1, Aug. 1, 2008
Ueki A, Yamaguchi M, Ueki H, et al. *Polyclonal human T-cell activation by silicate in vitro*. Immunology. 1994; 82:332-5.
Lee S, Hayashi H, Maeda M, Chen Y, Matsuzaki H, Takei-Kumagai N, Nishimura Y, Fujimoto W, Otsuki T. *Environmental factors producing autoimmune dysregulation—chronic activation of T cells caused by silica exposure. Immunobiology* 217 (2012) 743-748 Kusaka, Yasumitsu Nishimura and Takemi Otsuki (2014).
*Immunostimulation by Silica Particles and the Development of Autoimmune Dysregulation, Immune Response Activation*, Dr. Ht Duc (Ed.), InTech, DOI: 10.5772/57544.
Hayashi H, Miura Y, Maeda M, Murakami S, Kumagai N, Nishimura Y, Kusaka M, Urakami K, Fujimoto W, Otsuki T. *Reductive alteration of the regulatory function of the CD4(+)CD25(+) T cell fraction in silicosis patients*. International Journal of Immuno-pathology and Pharmacology 2010; 23(4) 1099-109.
Bastos, C. A. P.; Faria, N. J. R.; Powell, J. J.; Vis, B. M. Materials and methods relating to stabilised polymeric silicate compositions. WO2015121666, Aug. 20, 2015.
Bruggraber, S. F. A.; Faria N. J. R.; Pereira, D. I. A.; Powell, J. J. Ligand modified poly oxo-hydroxy metal ion materials, theirs uses and processes for their preparation. EP 2 125 847 B1, Feb. 6, 2008.
An, X., Y. Jin, M. J. Philbrick, J. Wu, A. Messmer-Blust, X. Song, B. L. Cully, P. He, M. Xu, and H. S. Duffy. 2012. Endothelial Cells Require Related Transcription Enhancer Factor-1 for Cell-Cell Connections Through the Induction of Gap Junction Proteins. Arteriosclerosis, thrombosis, and vascular biology. 32:1951-1959.
Chakraborty, A. K., and A. Weiss. 2014. Insights into the initiation of TCR signaling. Nature Immunology. 15:798-807.
Fathman, C. G., and N. B. Lineberry. 2007. Molecular mechanisms of CD4+ T-cell anergy. Nature Reviews Immunology. 7:599-609.
Love, P. E., and S. M. Hayes. 2010. ITAM-mediated signaling by the T-cell antigen receptor. Cold Spring Harbor perspectives in biology. 2:a002485.
Rossy, J., D. J. Williamson, and K. Gaus. 2012. How does the kinase Lck phosphorylate the T cell receptor? Spatial organization as a regulatory mechanism. Frontiers in immunology. 3:167.
Solan, J. L., M. D. Fry, E. M. TenBroek, and P. D. Lampe. 2003. Connexin43 phosphorylation at S368 is acute during S and G2/M and in response to protein kinase C activation. Journal of Cell Science. 116:2203-2211.
Wang, H., T. A. Kadlecek, B. B. Au-Yeung, H. E. S. Goodfellow, L.-Y. Hsu, T. S. Freedman, and A. Weiss.

2010. ZAP-70: an essential kinase in T-cell signaling. Cold Spring Harbor perspectives in biology. 2:a002279.

Becker J C, Schrama D. The dark side of cyclophosphamide: cyclophosphamide-mediated ablation of regulatory T cells. J Invest Dermatol. 2013 June; 133(6): 1462-5.

Crotty, S. 2015. A brief history of T cell help to B cells. *Nature Reviews Immunology*. 15:185-189.

Elgueta, R., M. J. Benson, V. C. De Vries, A. Wasiuk, Y. Guo, and R. J. Noelle. 2009. Molecular mechanism and function of CD40/CD40L engagement in the immune system. *Immunological reviews*. 229:152-172.

Gauthy, E., J. Cuende, J. Stockis, C. Huygens, B. Lethé, J.-F. Collet, G. Bommer, P. G. Coulie, and S. Lucas. 2013. GARP is regulated by miRNAs and controls latent TGF-β1 production by human regulatory T cells. *PloS one*. 8:e76186.

Geginat, J., M. Paroni, S. Maglie, J. S. Alfen, I. Kastirr, P. Gruarin, M. De Simone, M. Pagani, and S. Abrignani. 2015. Plasticity of human CD4 T cell subsets. *CD4+ T cell differentiation in infection: amendments to the Th1/Th2 axiom*:67.

Jugdaohsingh R, Reffitt D M, Oldham C, Day J P, Fifield L K, Thompson R P H, Powell J J. 2000. Oligomeric but not monomeric silica prevents aluminum absorption in humans. *American Journal of Clinical Nutrition*. 71:944-949.

Sakaguchi, S., M. Miyara, C. M. Costantino, and D. A. Hafler. 2010. FOXP3+ regulatory T cells in the human immune system. *Nature Reviews Immunology*. 10:490-500.

Sripanyakorn S et al., The comparative absorption of silicon from different foods and food Supplements. *British Journal of Nutrition* (2009), 102, 825-834.

Stockis, J., D. Colau, P. G. Coulie, and S. Lucas. 2009. Membrane protein GARP is a receptor for latent TGF-β on the surface of activated human Treg. *European journal of immunology*. 39:3315-3322.

The invention claimed is:

1. A method for the treatment of infection comprising administering to a subject in need thereof a composition comprising silica particles having a mean diameter between 0.5 and 5 nm, wherein administration of the composition activates T lymphocytes in the subject, wherein the T lymphocytes are CD4 and/or CD8 T lymphocytes, and wherein activation of the T lymphocytes is characterised by an increase in expression of CD69 and/or CD25 by the T lymphocytes by at least 20% as compared to unstimulated baseline control, thereby treating the infection in the subject, wherein the infection is a bacterial infection or a viral infection.

2. The method of claim 1, wherein the increase in expression of CD69 and/or CD25 is by at least 30% as compared to unstimulated baseline control.

3. The method of claim 1, wherein the lymphocyte activation comprises inducing an inflammatory Th1 type response.

4. The method of claim 1, wherein activation of the lymphocytes comprises:

(a) increasing expression of one or more further markers selected from CD40L, LAP/GARP, and/or FoxP3; and/or (b) increasing expression of IFN-γ.

5. The method of claim 1, wherein the composition substantially does not induce lymphocyte cell proliferation.

6. The method of claim 1, wherein the silica particles have a mean diameter between 2 and 5 nm.

7. The method of claim 1, wherein:

(a) the composition comprises one or more stabilising agents, optionally selected from polyols, sugars and/or quarternary ammonium salts; or (b) the composition does not comprise a stabilising agent.

8. The method of claim 1, wherein the silica composition is obtainable by precipitation.

9. The method of claim 1, wherein the infection follows treatment of cancer.

10. The method of claim 1, wherein the method comprises producing the composition of silica particles by in situ synthesis prior to administration to the subject.

11. The method of claim 10, wherein the in situ synthesis comprises:

(a) mixing (i) a silicate solution at pH>10.5 and (ii) an acidic buffer solution to produce a colloidal silica composition having a pH between 4.0 and 8.5;

(b) mixing (i) a silicate solution at pH>10.5 and (ii) an acidic buffer solution to produce a colloidal silica composition having a pH between 4.0 and 6.5 in a batch in situ synthesis process; or (c) mixing (i) a silicate solution at pH>10.5 and (ii) an acidic buffer solution to produce a colloidal silica composition having a pH between 6.5 and 8.5 in a flow in situ synthesis process.

12. The method of claim 11, wherein the method comprises administering the colloidal silica composition to the subject less than 12 minutes from mixing the solutions.

13. The method of claim 1, wherein the composition is administered intravenously.

14. The method of claim 13, wherein the acidic solution comprises hydrochloric acid, a carboxylic acid, or an acidic amino acid.

15. The method of claim 1, wherein the infection follows a burn, a wound, sunburn, psoriasis, eczema, and/or dermatitis.

16. The method of claim 1, wherein the infection is a bacterial infection.

17. The method of claim 1, wherein the infection is a viral infection.

18. The method of claim 1, wherein the subject is a human subject.

19. The method of claim 1, wherein the subject is a non-human animal.

20. The method of claim 19, wherein the non-Human animal is a dog, a cat, or a horse.

* * * * *